US010357269B2

(12) United States Patent
Worrell et al.

(10) Patent No.: US 10,357,269 B2
(45) Date of Patent: Jul. 23, 2019

(54) DEVICES AND METHODS FOR INCREASING ROTATIONAL TORQUE DURING END EFFECTOR ARTICULATION

(71) Applicant: Ethicon Endo-Surgery, LLC, Guaynabo, PR (US)

(72) Inventors: Barry C. Worrell, Centerville, OH (US); Jason R. Lesko, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 536 days.

(21) Appl. No.: 14/959,361

(22) Filed: Dec. 4, 2015

(65) Prior Publication Data
US 2017/0156747 A1 Jun. 8, 2017

(51) Int. Cl.
*A61B 17/29* (2006.01)
*A61B 17/28* (2006.01)
*A61B 18/14* (2006.01)
*A61B 17/00* (2006.01)

(52) U.S. Cl.
CPC .......... *A61B 17/29* (2013.01); *A61B 17/282* (2013.01); *A61B 17/2816* (2013.01); *A61B 17/2909* (2013.01); *A61B 18/1445* (2013.01); *A61B 2017/003* (2013.01); *A61B 2017/2927* (2013.01); *A61B 2017/2929* (2013.01); *A61B 2018/1455* (2013.01)

(58) Field of Classification Search
CPC ............ A61B 2017/2901; A61B 17/29; A61B 2017/2902; A61B 2017/2903; A61B 17/282
See application file for complete search history.

(56) References Cited

U.S. PATENT DOCUMENTS

2008/0294191 A1* 11/2008 Lee .................. A61B 17/00234
606/205
2012/0078247 A1 3/2012 Worrell et al.
(Continued)

OTHER PUBLICATIONS

U.S. Appl. No. 14/658,944 entitled "Methods and Devices for Actuating Surgical Instruments", filed Mar. 16, 2015.
(Continued)

*Primary Examiner* — Kathleen S Holwerda
*Assistant Examiner* — Christina C Lauer
(74) *Attorney, Agent, or Firm* — Mintz Levin Cohn Ferris Glovsky and Popeo, P.C.

(57) ABSTRACT

Devices and methods for increasing rotational torque during end effector articulation are provided. In general, a surgical device can include an end effector configured to articulate. The end effector can be configured to move between different angular orientations relative to an elongate shaft of the device having the end effector at a distal end thereof. The elongate shaft and the end effector can be configured to be rotated relative to a handle portion of the device. The device can include at least one friction member configured to provide increased resistance to rotation of the elongate shaft and the end effector when the end effector is articulated as compared to when the end effector is not articulated. The at least one friction member can thus be configured to increase rotational torque when the end effector is articulated as compared to when the end effector is not articulated.

14 Claims, 21 Drawing Sheets

(56) References Cited

U.S. PATENT DOCUMENTS

2013/0023868 A1\*  1/2013  Worrell ............ A61B 17/07207
                                                            606/33
2015/0209059 A1   7/2015  Trees et al.

OTHER PUBLICATIONS

U.S. Appl. No. 14/659,037 entitled "Flexible Neck for Surgical Instruments", filed Mar. 16, 2015.
International Search Report and Written Opinion for Intl. App. PCT/US2016/063911 dated Mar. 15, 2017 (9 pages).

\* cited by examiner

DEVICES AND METHODS FOR INCREASING ROTATIONAL TORQUE DURING END EFFECTOR ARTICULATION

FIELD

Devices and methods are provided for increasing rotational torque during end effector articulation.

BACKGROUND

Endoscopic surgical instruments are often preferred over traditional open surgical devices since a smaller incision, or incisions, associated with endoscopic surgical techniques tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, radiofrequency (RF), laser, etc.).

In order to provide for better maneuverability and positioning of the end effector, many surgical devices enable articulation of the end effector as well as rotation of the shaft having the end effector at a distal end thereof. Articulation and rotation of the end effector can enable the surgeon to reach tissue that may otherwise be inaccessible. While in an articulated state, a load on the end effector creates a moment arm that can cause undesired rotation of the end effector.

Accordingly, there remains a need for increasing rotational torque during end effector articulation.

SUMMARY

In general, devices and methods for increasing rotational torque during end effector articulation are provided.

In one aspect, a surgical device is provided that in one embodiment includes a handle, an elongate shaft extending distally from the handle and being configured to rotate relative to the handle, and an end effector at a distal end of the elongate shaft and having first and second jaws configured to engage tissue therebetween. The end effector is configured to articulate relative to the elongate shaft such that the end effector is angularly oriented relative to the elongate shaft. When the end effector is articulated relative to the elongate shaft, a force required to rotate the elongate shaft relative to the handle is greater than a force required to rotate the elongate shaft relative to the handle when the end effector is in a non-articulated, substantially linear orientation relative to the elongate shaft.

The surgical device can vary in any number of ways. For example, the surgical device can include a friction member disposed within the handle and configured to apply an increased frictional force to the elongate shaft when the end effector is articulated as compared to when the end effector is in the non-articulated, substantially linear orientation. The frictional force can be configured to increase in proportion to increasing articulation of the end effector, the friction member can be configured to increasingly deform in shape in proportion to increasing articulation of the end effector, the friction member can be elastomeric, the surgical device can include an actuator configured to be actuated to cause the articulation of the end effector and the actuation of the actuator can also cause compression of the friction member, and/or the surgical device can include an actuator configured to be actuated to cause the rotation of the elongate shaft. In embodiments in which the surgical device includes the actuator, the force required to rotate the elongate shaft relative to the handle when the end effector is articulated relative to the elongate shaft can be applied to the actuator, and the force required to rotate the elongate shaft relative to the handle when the end effector is in the non-articulated, substantially linear orientation relative to the elongate shaft can be applied to the actuator such that a greater force is required to be applied to the actuator to rotate the elongate shaft when the end effector is articulated relative to the elongate shaft.

For another example, the surgical device can include a friction member disposed within the handle and configured to resist rotation of the elongate shaft when the end effector is articulated relative to the elongate shaft. The friction member can be configured to not resist rotation of the elongate shaft when the end effector is in the non-articulated, substantially linear orientation, and/or the surgical device can include an actuation mechanism configured to move relative to the elongate shaft to cause the articulation of the end effector, and/or the surgical device can include an actuator configured to be actuated to cause rotational movement of the actuator and thereby cause the articulation of the end effector. In embodiments in which the surgical device includes the actuation mechanism, the friction member can have one or more grooves formed therein that are configured to be locked with the actuation mechanism when the end effector is articulated relative to the elongate shaft and to be unlocked from the actuation mechanism when the end effector is in the non-articulated, substantially linear orientation. In embodiments in which the surgical device includes the actuator, the friction member can be operatively coupled to the actuator such that the rotational movement of the actuator causes rotational movement of the clutch mechanism.

For yet another example, the end effector can be configured to rotate with the elongate shaft relative to the handle.

In another embodiment, a surgical device includes an elongate shaft having a longitudinal axis, an end effector at a distal end of the elongate shaft, a first actuator configured to be actuated to cause rotation of the elongate shaft and the end effector about the longitudinal axis of the elongate shaft, a second actuator configured to be actuated to angularly adjust the end effector relative to the longitudinal axis of the elongate shaft, and a friction member configured to adjust an amount of force required to be applied to the first actuator to cause the rotation of the elongate shaft and the end effector based on an angle of the end effector relative to the longitudinal axis of the elongate shaft. The end effector is configured to manipulate tissue during performance of a surgical procedure.

The surgical device can have any number of variations. For example, the greater the angle of the end effector relative to the longitudinal axis of the elongate shaft, the greater the amount of force the friction member can be configured to require to be applied to the first actuator to cause the rotation of the elongate shaft and the end effector. For another example, the friction member can include a brake mechanism configured to increasingly deform in shape the greater the angle of the end effector relative to the longitudinal axis of the elongate shaft, and the amount of force can correspond to an a degree of the brake mechanism's shape deformation. For yet another example, the friction member can include a clutch mechanism configured to move between a locked configuration and an unlocked configuration based on the angle of the end effector relative to the longitudinal axis of the elongate shaft, and the amount of force can correspond to whether the clutch mechanism is in the locked configuration or the unlocked configuration. For still another example, the surgical device can include a handle, the elongate shaft can extend distally from the handle, and the friction member can be disposed within the handle.

In another aspect, a method for treating tissue is provided that in one embodiment includes applying a first force to a first actuator on a handle of a device to rotate an elongate shaft of the device relative to the handle, actuating a second actuator on the handle to cause an end effector at a distal end of the elongate shaft to articulate relative to the elongate shaft, and manipulating the device to cause the end effector to effect tissue. With the end effector articulated relative to the elongate shaft, the elongate shaft is prevented from rotating relative to the handle until a second force that is greater than the first force is applied to the first actuator.

The method can have any number of variations. For example, the first force can be applied to the first actuator with the end effector not being articulated relative to the elongate shaft. For another example, the first actuator can include a rotation knob, the first force can include a first rotational force that rotates the rotation knob, the second actuator can include an articulation knob, and actuating the second actuator can include rotating the articulation knob.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Figure 1:
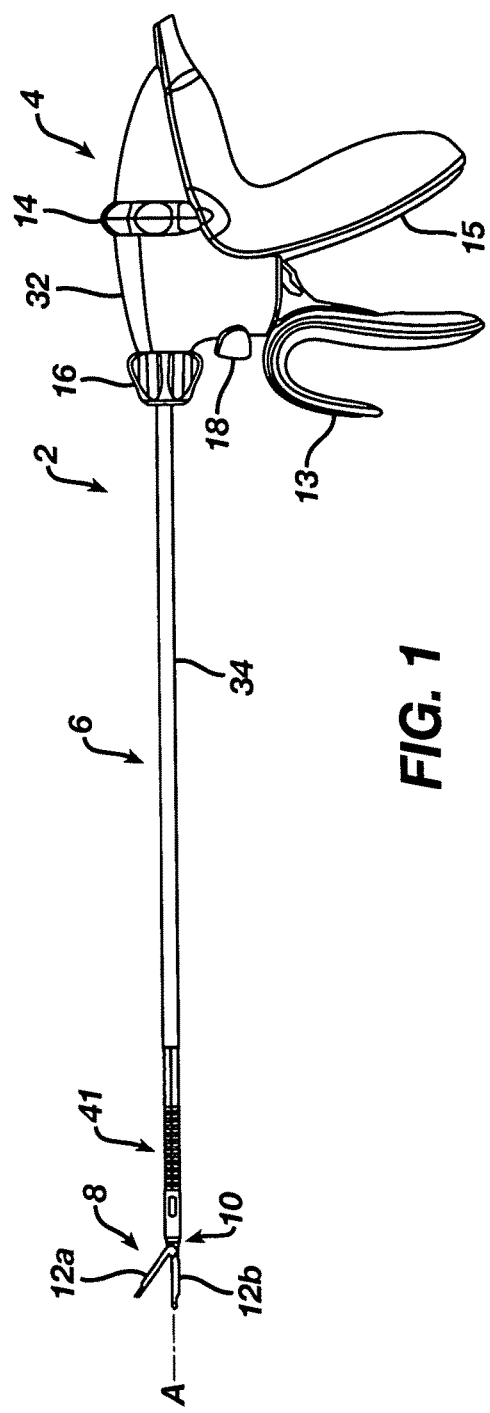
FIG. 1 is a side view of one embodiment of a surgical device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Devices and methods for increasing rotational torque during end effector articulation are provided. In general, a surgical device can include an end effector configured to articulate. The end effector can be configured to move between different angular orientations relative to an elongate shaft of the device having the end effector at a distal end thereof. The elongate shaft and the end effector can be configured to be rotated relative to a handle portion of the device. The device can include at least one friction member configured to provide increased resistance to rotation of the elongate shaft and the end effector when the end effector is articulated as compared to when the end effector is not articulated. The at least one friction member can thus be configured to increase rotational torque when the end effector is articulated as compared to when the end effector is not articulated. In other words, the at least one friction member can be configured to increase an amount of force required to rotate the elongate shaft and the end effector, e.g., an amount of force required to be applied by a user to the device to cause rotation of the elongate shaft and the end effector, when the end effector is articulated as compared to when the end effector is not articulated. The end effector may thus be less likely to unintentionally rotate when articulated since a greater rotational torque force must be applied to the device to cause rotation of the elongate shaft and end effector when the end effector is articulated as compared to when the end effector is not articulated, which may allow for more precise control of end effector position during performance of a surgical procedure and thus help the end effector manipulate tissue as intended without losing grip on the tissue and/or without damaging any adjacent tissue or any other adjacent structures.

Figure 2:
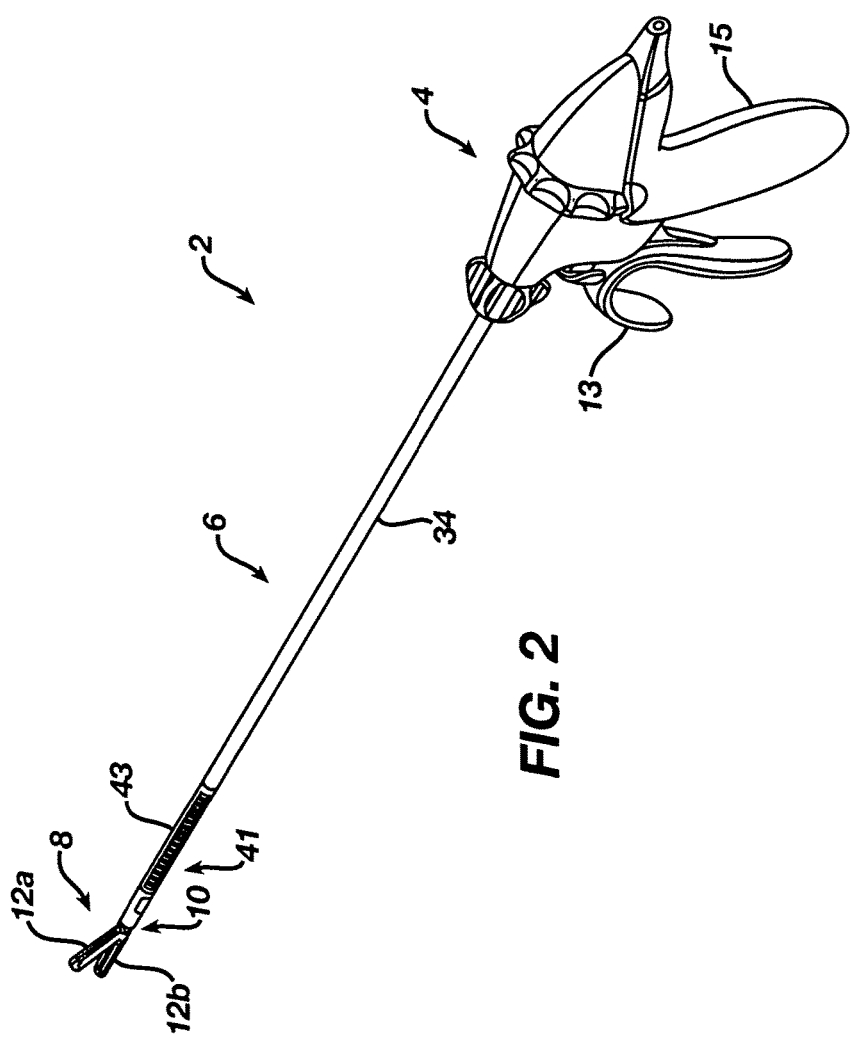
FIG. 2 is a perspective view of the device of FIG. 1.
Figure 3:
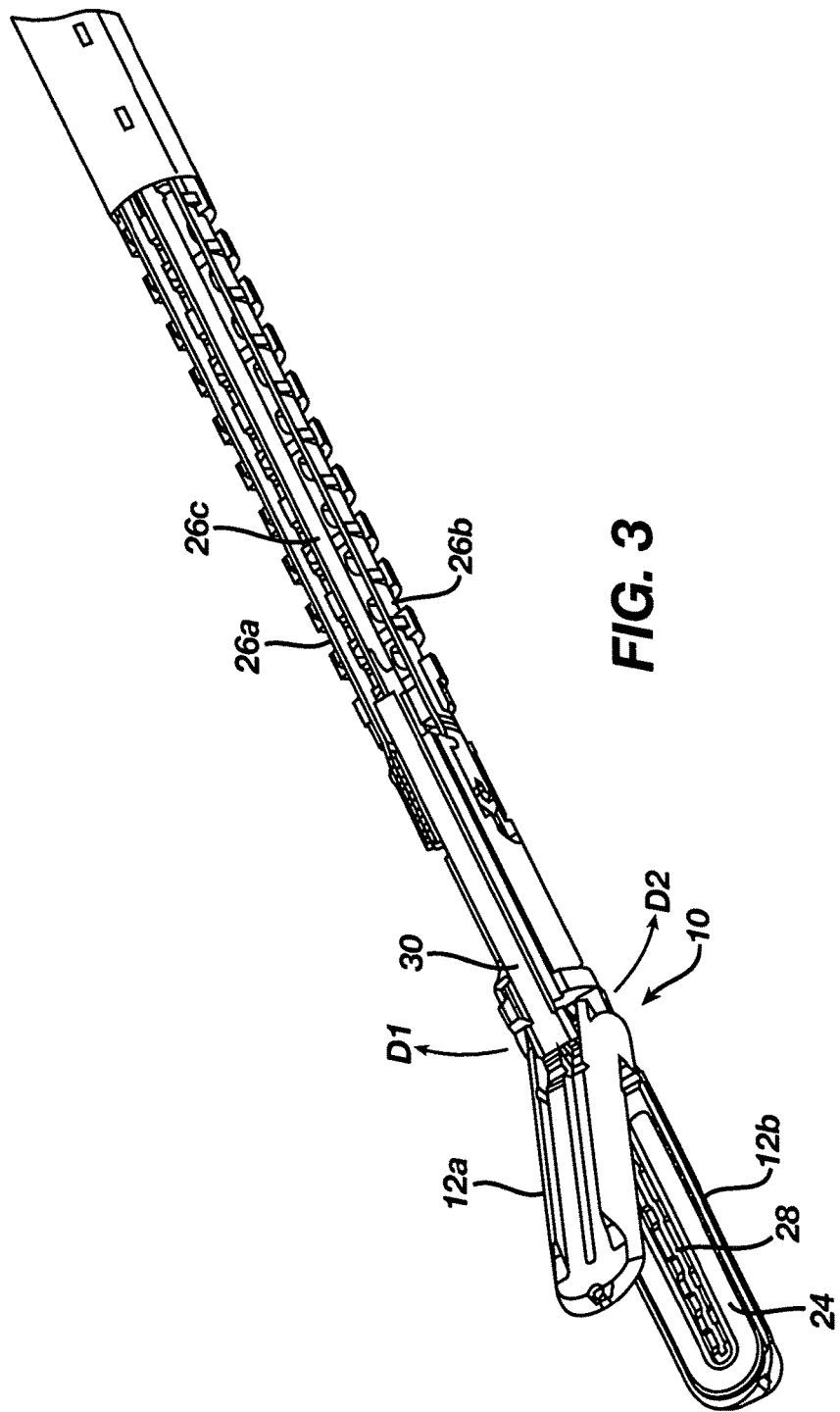
FIG. 3 is a perspective view of a distal portion of the device of FIG. 1 with select elements of the device omitted for clarity of illustration.

FIG. 1 illustrates one embodiment of a surgical device 2 that can include a proximal handle portion 4 having a shaft assembly 6 extending distally therefrom. As also shown in FIGS. 2 and 3, the device 2 can include a working element 8, also referred to herein as an "end effector," coupled to a distal end of the shaft assembly 6. The end effector 8 can be coupled to the shaft assembly 6 at a pivot joint 10. A proximal end of the end effector 8 can be pivotally coupled to the joint 10 at the distal end of the shaft assembly 6.

The end effector 8 can have a variety of sizes, shapes, and configurations. As shown in FIGS. 1-3, the end effector 8, including the first and second jaws 12a, 12b, can be disposed at a distal end of the surgical device 2. The end effector 8 in this illustrated embodiment includes a tissue grasper having a pair of opposed jaws 12a, 12b configured to move between open and closed positions. The end effector 8 can have other configurations, e.g., scissors, a babcock, a retractor, etc. In an exemplary embodiment, the end effector 8 can be rigid. The end effector 8 can include the first, top, or upper jaw 12a and the second, bottom, or lower jaw 12b pivotally connected together at the pivot joint 10.

One or both of the jaws 12a, 12b can include electrodes 24 on tissue engagement surfaces thereof. The electrodes 24 can be configured to contact tissue positioned between the jaws 12a, 12b and to apply energy thereto. The electrodes 24 in this illustrated embodiment include a U-shaped electrode on the bottom jaw 12b and a corresponding U-shaped electrode (obscured in the figures) on the upper jaw 12a, but the electrodes 24 can be arranged in any of a variety of ways on the upper jaw 12a and/or the lower jaw 12b. The electrodes 24 of the device 2 can generally be configured and used similar to electrodes described in U.S. patent application Ser. No. 14/658,944 entitled "Methods and Devices for Actuating Surgical Instruments" filed on Mar. 16, 2015, which is hereby incorporated by reference in its entirety.

The handle portion 4 can have a variety of sizes, shapes, and configurations. The handle portion 4 can include a main housing 32, which can house a variety of elements therein and can have some elements accessible outside thereof, such as a first actuator 13, a second actuator 14, a third actuator 16, and a fourth actuator 18.

The first actuator 13 can be configured to effect the opening and closing of the opposed jaws 12a, 12b, e.g., movement of the jaws 12a, 12b toward and away from one another. The jaws 12a, 12b in FIGS. 1-3 are shown in the open position. As in this illustrated embodiment, the upper jaw 12a can be configured to move relative to the bottom jaw 12b, which can remain stationary relative to the shaft assembly 6, to effect the opening and closing of the end effector 8. In other embodiments, in order to effect opening and closing of the end effector, the bottom jaw can be configured to move relative to the upper jaw, or both the upper and lower jaws can be configured to move relative to the shaft assembly.

The first actuator 13 can be configured to translate a cutting element (obscured in the figures) (e.g., a knife, a blade, etc.) along the end effector 8. The cutting element can be configured to cut tissue positioned between the jaws 12a, 12b, as will be appreciated by a person skilled in the art. As shown in FIG. 3, the jaws 12a, 12b can include an elongate slot 28 in the tissue engagement surfaces thereof (the slot in the upper jaw 12a is obscured in FIG. 3) through which the cutting element can be configured to slide.

In an exemplary embodiment, the first actuator 13 can include a gripper arm, also referred to herein as a "closure trigger" and a "movable handle." The closure trigger 13 can, in other embodiments, have different sizes, shapes, and configurations, e.g., no thumb rests, multiple finger loops, different arcuate shape, etc. As in this illustrated embodiment, the closure trigger 13 can be pivotally attached to the main housing 32. The closure trigger 13 can be configured to move toward and away from the main housing 32, thereby causing opening and closing of the end effector 8, as discussed further below.

The second actuator 14 can be configured to effect articulation of the end effector 8, e.g., movement of both jaws 12a, 12b in a same direction relative to a longitudinal axis A of the shaft assembly 6. The articulation can be independent of the opening and closing of the jaws 12a, 12b. The end effector 8 in FIGS. 1-3 is shown in an unarticulated position, e.g., at a substantially zero angle relative to the longitudinal axis A so as to be in a substantially linear orientation along the longitudinal axis A. A person skilled in the art will appreciate that the end effector 8 may not be at precisely at a zero angle relative to the longitudinal axis A of the shaft assembly 6 but nevertheless be considered to be at a substantially zero angle relative to the longitudinal axis A of the shaft assembly 6 due to any one or more factors, such as manufacturing tolerance and sensitivity of angle measurement devices. The second actuator 14 can be operatively connected to an actuation mechanism, which can be disposed within the main housing 32 and is discussed further below, such that actuation of the second actuator 14, e.g., manual movement thereof by a user, can cause articulation of the end effector 8. In an exemplary embodiment, the second actuator 14 can be configured to be actuated so as to cause the jaws 12a, 12b to articulate in opposite directions D1, D2 (shown in FIG. 3) relative to the longitudinal axis A.

Figure 5:
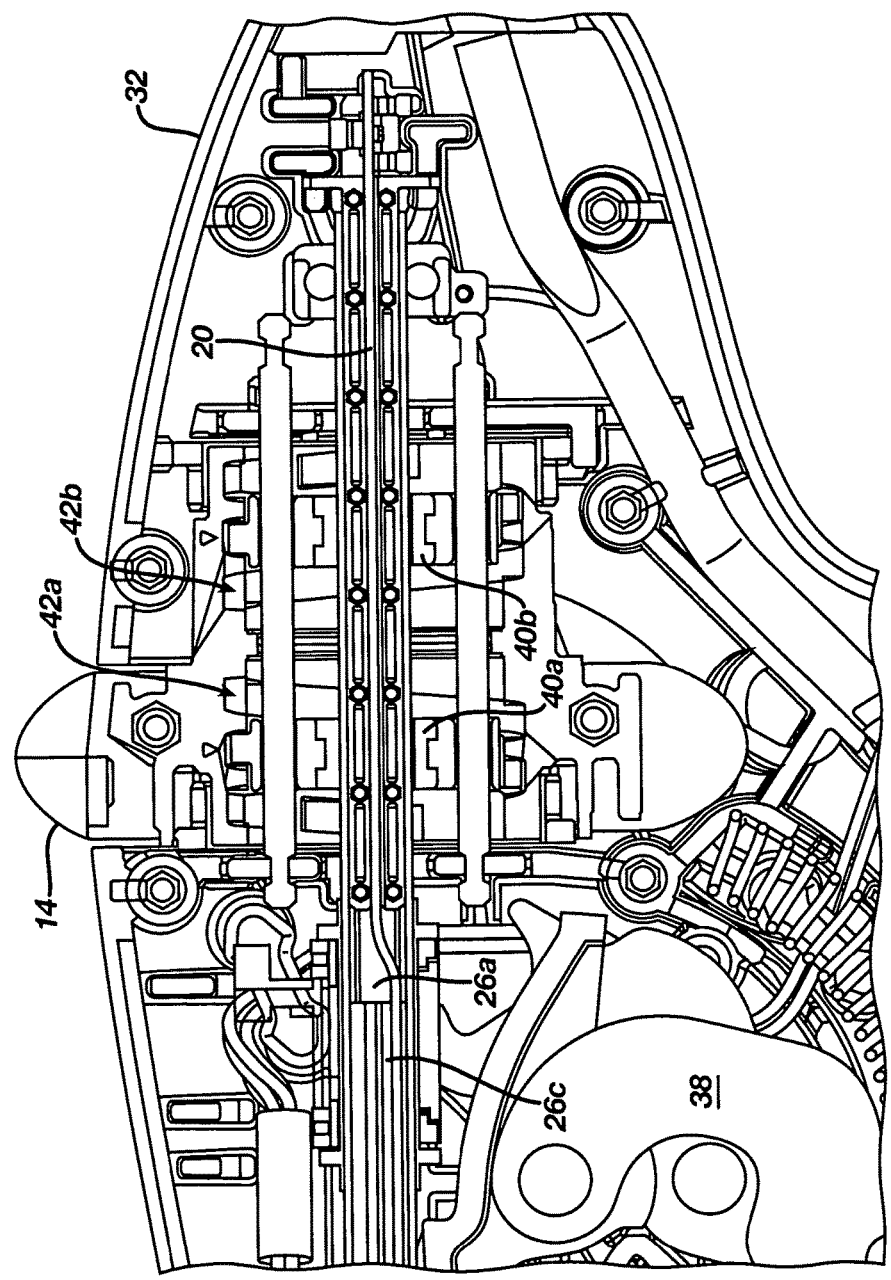
FIG. 5 is a side cross-sectional view of another portion of the handle portion of the device of FIG. 1.

The second actuator 14 can have a variety of sizes, shapes, and configurations. As in this illustrated embodiment, the second actuator 14 can include a rotatable knob. Rotation of the second actuator 14 in one direction (e.g., clockwise) can be configured to cause articulation of the end effector 8 in the first direction D1 (e.g., right) and rotation of the second actuator 14 in the opposite direction (e.g., counterclockwise) can be configured to cause articulation of the end effector 8 in the second direction D2 (e.g., left). The knob 14 can be rigid, e.g., can be formed of a rigid material. The knob 14 can include a moveable ring, as shown in FIG. 5. The knob 14 can include one or more finger depressions on an exterior surface thereof, as in this illustrated embodiment. The finger depressions can facilitate manual movement of the knob 14 using one or more fingers seated in the finger depressions. As in this illustrated embodiment, the finger depressions can extend around an entire circumference of the knob's exterior surface.

The third actuator 16 can be configured to rotate the shaft assembly 6 and the end effector 8 about the longitudinal axis A of the shaft assembly 6. The third actuator 16 includes a rotatable knob in this illustrated embodiment that can be rotated about the longitudinal axis A, but the third actuator 16 can have a variety of other configurations, e.g., a lever, a button, a movable handle, etc. As in this illustrated embodiment, the third actuator 16 can be configured to continuously and repeatedly rotate the shaft assembly 6 and the end effector 8 360° in both clockwise and counterclockwise directions. In other words, the shaft assembly 6 can be configured for unlimited bi-directional rotation. As will be appreciated by a person skilled in the art, the shaft assembly 6 and the end effector 8 can be rotated less than 360° as desired during performance of a surgical procedure (e.g., rotated 20°, rotated 90°, rotated 150°, etc.) and can be rotated more than 360° as desired during performance of a surgical procedure (e.g., rotated 450°, rotated 480°, rotated 720°, etc.).

As in this illustrated embodiment, the surgical device 2 can be powered and be configured as an electrosurgical tool configured to apply energy to tissue, such as radiofrequency (RF) energy. The handle portion 4 can have a power cord (not shown) extending proximally therefrom that can be configured to supply electrical power to the device 2, such as by connecting to a generator, by plugging into an electrical outlet, etc. In other embodiments, the surgical device can be unpowered, e.g., not be configured to apply energy to tissue.

The fourth actuator 18 can be configured to turn on and off the application of the energy, which can be delivered to tissue via the electrodes 24. The fourth actuator 18 includes a button in this illustrated embodiment, but the fourth actuator 18 can have other configurations, e.g., a knob, a lever, a movable handle, a switch, etc. In other embodiments, the fourth actuator 18, instead of the first actuator 13, can be configured to translate the cutting element.

The shaft assembly 6 can have a variety of sizes, shapes, and configurations. The shaft assembly 6 can have any longitudinal length, although in an exemplary embodiment it can be long enough to allow the handle portion 4 to be manipulated outside a patient's body while the shaft assembly 6 extends through an opening in the body with the end effector 8 disposed within a body cavity, e.g., have a longitudinal length in a range of about 25 to 50 cm, such as a longitudinal length of about 33 cm. In this way, the end effector 8 can be easily manipulated when the device 2 is in use during a surgical procedure. The shaft assembly 6 can have any diameter. For example, the shaft assembly's diameter can be less than or equal to about 15 mm, e.g., less than or equal to about 10 mm, less than or equal to about 7 mm, less than or equal to about 5 mm, etc., which can allow for insertion of the shaft assembly 6 through an minimally invasive access device, such as during a laparoscopic surgical procedure. The end effector 8 mated to the shaft assembly's distal end can have a diameter equal to or less than the shaft assembly's diameter, at least when the jaws 12a, 12b are in the closed position, which can facilitate insertion of the device's distal portion into a patient's body.

As in this illustrated embodiment, the shaft assembly 6 can include an outer elongate shaft 34 (also referred to herein an "outer shell") and at least one actuation shaft extending between the handle portion 4 and the end effector 8. The one or more actuation shafts can be configured to facilitate articulation of the end effector 8, to facilitate opening/closing of the end effector 8, and/or to facilitate movement of the cutting element along the end effector 8. As in this illustrated embodiment, as shown in FIG. 3, the device 2 can include first and second actuation shafts 26a, 26b configured to facilitate articulation of the end effector 8, and a third actuation shaft 26c configured to facilitate movement of the cutting element 26 along the end effector 8. In other embodiments, a surgical device can include any combination of the actuation shafts configured to facilitate articulation of the end effector, and movement of the cutting element along the end effector, e.g., only include the first and second actuation shafts; only include the third actuation shaft; include the first, second, and third actuation shafts; etc. The actuation shafts can each have relatively small diameters, which can facilitate their inclusion in a device configured to use in a minimally invasive surgical procedure.

The first, second, and third actuation shafts 26a, 26b, 26c can each have a variety of configurations. As in this illustrated embodiment, each of the actuation shafts 26a, 26b, 26c can include an elongate planar member. Examples of actuation shafts are further described in previously mentioned U.S. patent application Ser. No. 14/658,944 entitled "Methods and Devices for Actuating Surgical Instruments" filed on Mar. 16, 2015.

The first and second actuation shafts 26a, 26b can be operatively connected to the device's second actuator 14 to facilitate articulation of the end effector 8. The first and second actuation shafts 26a, 26b can be operatively connected to the device's second actuator 14 in a variety of ways. As in this illustrated embodiment, as shown in FIGS. 4-7, and as discussed further below, the device 2 can include first and second nuts 44a, 44b and first and second connection rods 22a, 22b. The second actuation shaft 22b is also shown as a standalone element in FIG. 8. The first nut 44a and the first connection rod 22a can be configured to operatively couple the first actuation shaft 26a to the second actuator 14, and the second nut 44b and the second connection rod 22b can be configured to operatively couple the second actuation shaft 22b to the second actuator 14.

The third actuation shaft 26c can be operatively connected to the device's fourth actuator 18 to facilitate movement of the cutting element through the end effector 8. The third actuation shaft 26c can be operatively connected to the first actuator 13 such that actuation of the first actuator 13 can be configured to cause movement of the third actuation shaft 26c and thereby move the cutting element along the end effector 8 and cause the jaws 12a, 12b to close (e.g., the end effector 8 to move to a closed position). The third actuation shaft 26c can have a compression member 30 (see FIG. 3) coupled to a distal end thereof. The compression member 30 can have the cutting element at a distal end thereof, as in this illustrated embodiment. The compression member 30 can be configured to translate along the end effector 8 in opposed channels (obscured in the figures) formed in the first and second jaws 12a, 12b to cause the jaws 12a, 12b to close, as the cutting element on the compression member 30 translates along the end effector 8. Examples of compression members are further described in U.S. Pat. Pub. No. 2015/0209059 entitled "Methods And Devices For Controlling Motorized Surgical Devices" filed on Jan. 28, 2014, which is hereby incorporated by reference in its entirety, and in previously mentioned U.S. Pat. Pub. No. 2012/0078247 entitled "Articulation Joint Features For Articulating Surgical Device" filed on Sep. 19, 2011.

Figure 4:
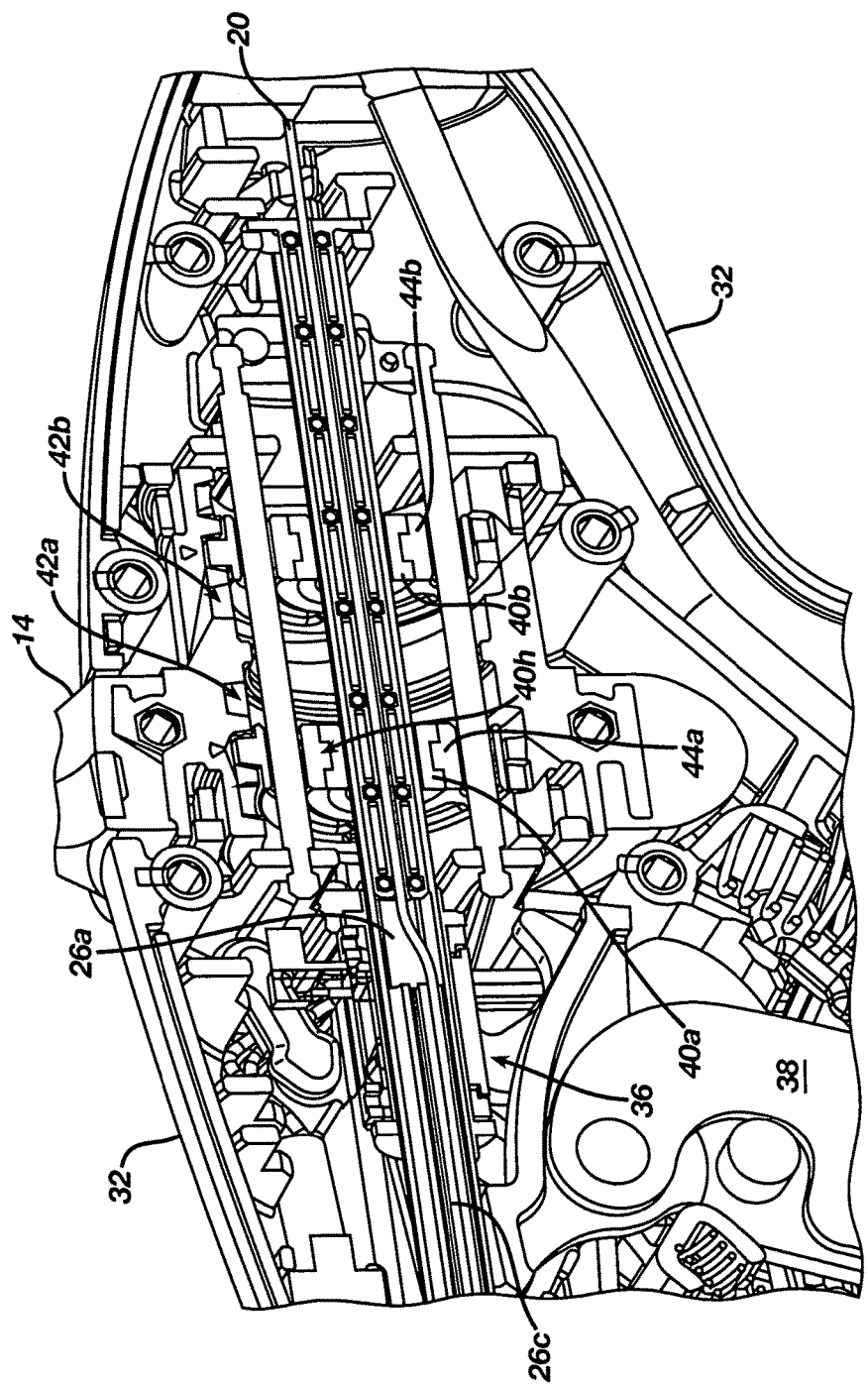
FIG. 4 is a perspective cross-sectional view of a portion of a handle portion of the device of FIG. 1.
Figure 6:
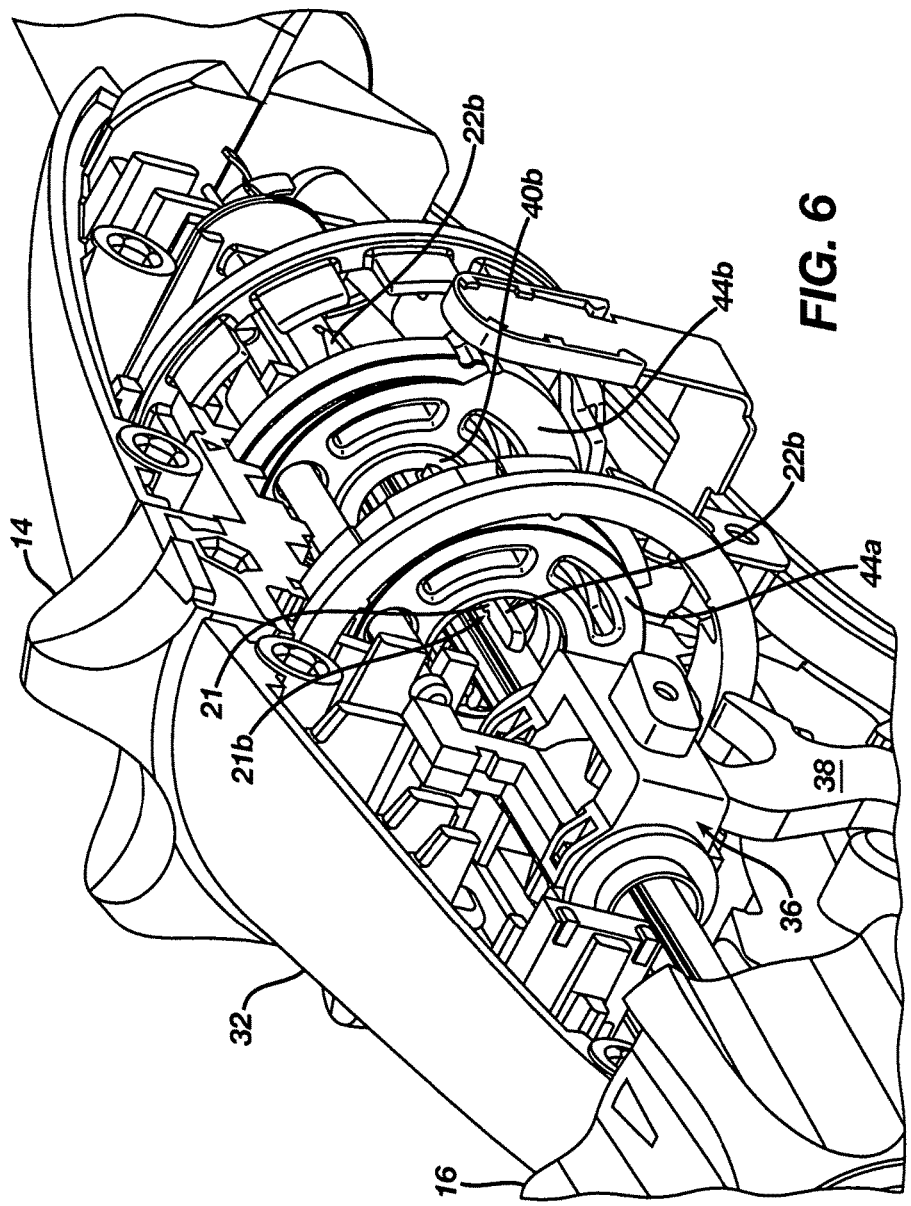
FIG. 6 is a perspective view of a portion of the handle portion of the device of FIG. 1 with select elements of the device omitted for clarity of illustration.

The third actuation shaft 26c can be operatively connected to the first actuator 13 in a variety of ways. As in this illustrated embodiment, as shown in FIGS. 4-6, the first actuator 13 can be operatively coupled to a closure mechanism 36 via a lever 38. Movement of the first actuator 13 toward the housing 32, e.g., toward a stationary handle 15 (see FIGS. 1 and 2) thereof, can be configured to cause pivoting motion of the lever 38, which can be configured to cause the closure mechanism 36 to move in a distal direction. The third actuation shaft 26c can be fixedly coupled to the closure mechanism 36, as shown in FIGS. 4 and 5, such that the distal movement of the closure mechanism 36 causes distal movement of the third actuation shaft 26c and of the compression member 30 coupled thereto, thereby causing end effector 8 closure and distal movement of the cutting element along the end effector 8. Likewise, movement of the closure trigger 13 away from the housing 32, e.g., away from the stationary handle 15, can cause proximal movement of the closure mechanism 36 and thereby cause the end effector 8 to open and the cutting element to move proximally along the end effector 8.

In other embodiments, instead of the first actuator 13 being configured to cause cutting element translation and end effector 8 closure, the device 2 can include one actuator (e.g., the first actuator 13) configured to effect end effector 8 closure and another actuator (e.g., a fifth actuator, not shown) configured to cause movement of the cutting element.

The fourth actuator 18 can be operatively connected to a conductive lead 20 (shown in FIGS. 4 and 5), which in this illustrated embodiment includes an RF cable, configured to be in electrical communication with the power cord and with the electrodes 24. The actuation of the fourth actuator 18, e.g., pushing the button, can be configured to close a circuit and thereby allow power to be provided to the RF cable 20, which can accordingly allow power to be supplied to the electrodes 24.

The device 2 can include a bend region 41 configured to facilitate articulation of the end effector 8. The bend region can include a flexible outer shell 43, shown in FIG. 2. The flexible outer shell 43 can, as a flexible member, be configured to flex or bend without cracking, breaking, or otherwise becoming damaged, which can facilitate articulation of the end effector 8. The flexible outer shell 43 can have an inner lumen extending therethrough, an upper spine extending longitudinally therealong, a lower spine extending longitudinally therealong, and a plurality of spaced ribs extending between the upper and lower spines on either side (e.g., left and right sides) of the flexible outer shell 43. The first, second, and third actuation shafts 26a, 26b, 26c and the RF cable 20 can each extend through the inner lumen of the flexible outer shell 43. Exemplary embodiments of flexible outer shells are further described in U.S. Pat. Pub. No. 2012/0078247 entitled "Articulation Joint Features For Articulating Surgical Device" filed on Sep. 19, 2011, and in U.S. application Ser. No. 14/659,037 entitled "Flexible Neck For Surgical Instruments" filed on Mar. 16, 2015, which are hereby incorporated by reference in their entireties.

Figure 9:
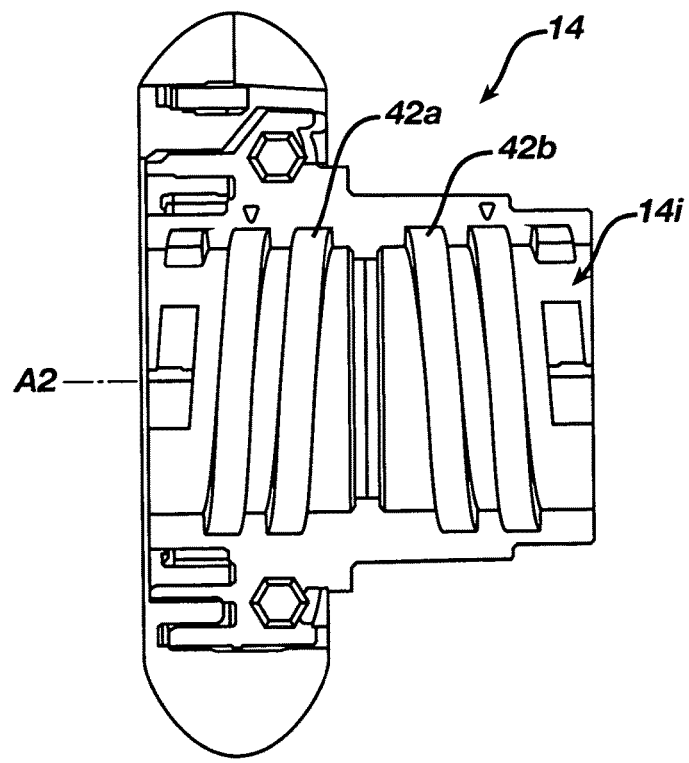
FIG. 9 is a side cross-sectional view of an actuator of the device of FIG. 1.

As mentioned above, the second actuator 14 can be configured to facilitate articulation of the end effector 8, which as also mentioned above, can include bending or flexing of the flexible outer shell 43. The actuation mechanism operatively connected to the second actuator 14 can have a variety of sizes, shapes, and configurations. As in this illustrated embodiment, the actuation mechanism can be coupled to the proximal handle portion 4 of the device 2 and can include the second actuator 14, which as described herein can be configured to be manually actuated by a user to effect articulation of the end effector 8. FIG. 9 illustrates the second actuator 14 as a standalone element in cross-section. As in this illustrated embodiment, the second actuator 14 can include a ring-shaped portion configured to be accessible to a user outside the main housing 32 and can include an elongate tubular portion extending proximally from the ring-shaped portion and being configured to be contained within the main housing 32. The second actuator 14 can thus be cannulated.

The second actuator 14 can include first and second threads 42a, 42b formed in an internal surface 14i thereof. The first thread 42a can be associated with the first actuation shaft 26a, and the second thread 42b can be associated with the second actuation shaft 26b, as discussed further below. The first and second threads 42a, 42b can be independent from one another, as in this illustrated embodiment, with each of the first and second threads 42a, 42b defining separate paths. The first and second threads 42a, 42b can wind in opposite directions around the second actuator 14, e.g., one left-handed and one right-handed. The first and second threads 42a, 42b can have any length around the second actuator's internal surface 14i. In an exemplary embodiment, the first and second threads 42a, 42b can have the same length around the second actuator's internal surface 14i, which may facilitate symmetrical articulation of the end effector 8. The first and second threads 42a, 42b in this illustrated embodiment includes grooves configured to mate with corresponding protrusions configured to slide within the grooves. In other embodiments, the first and second threads 42a, 42b of the second actuator 14 can include protrusions configured to slidably mate with corresponding grooves.

Figure 10:
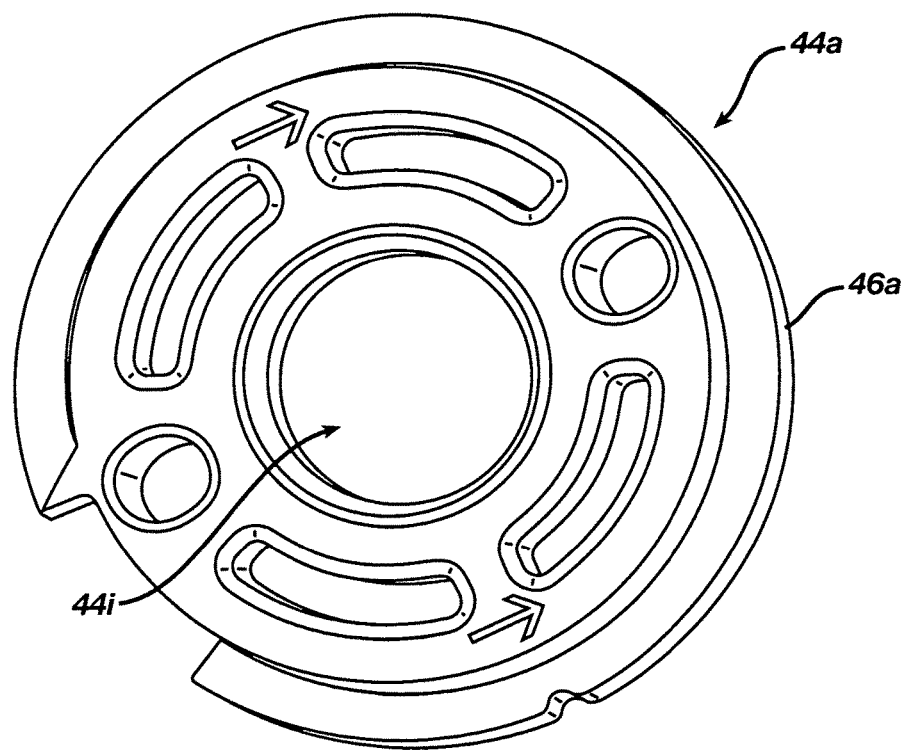
FIG. 10 is a perspective view of a drum of the device of FIG. 1.
Figure 11:
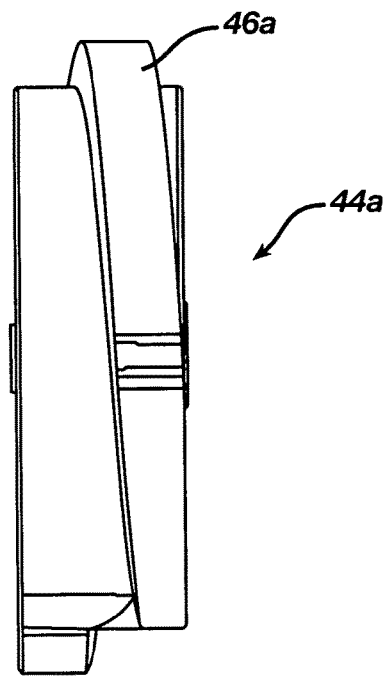
FIG. 11 is a side view of the drum of FIG. 10.
Figure 12:
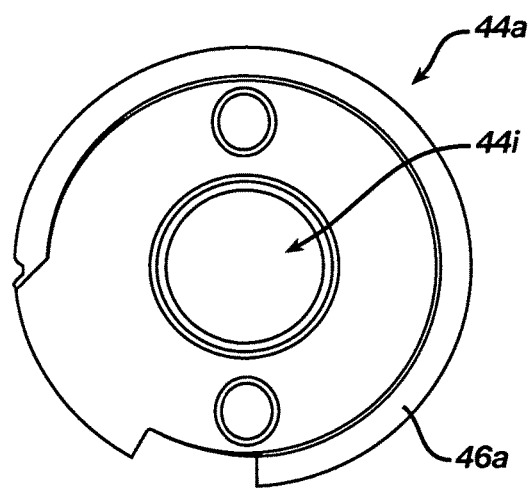
FIG. 12 is an end view of the drum of FIG. 10.
Figure 13:
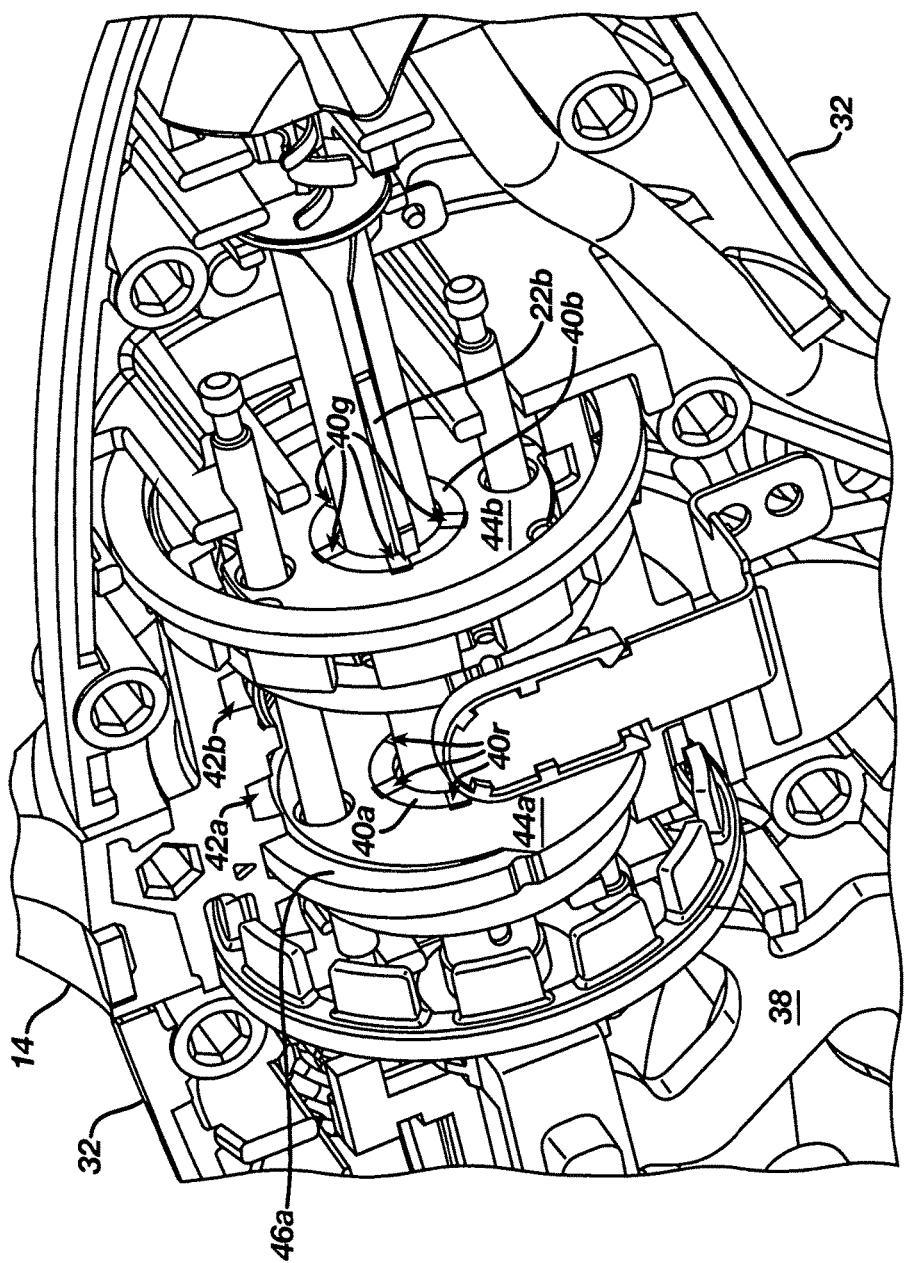
FIG. 13 is another perspective view of a portion of the handle portion of the device of FIG. 1 with select elements of the device omitted for clarity of illustration.

The actuation mechanism can include the first and second nuts 44a, 44b, also referred to herein as "drums," configured to movably mate with the second actuator 14. The first and second drums 44a, 44b can have a variety of sizes, shapes, and configurations. The first nut 44a can be associated with the first actuation shaft 26a, and the second nut 44b can be associated with the second actuation shaft 26b, as discussed further below. As in this illustrated embodiment, each of the first and second drums 44a, 44b can be generally cylindrical in shape and can be cannulated. The first and second drums 44a, 44b can each be configured to be disposed within the cannulated interior of the second actuator 14, as illustrated in FIGS. 4-7 (the first drum 44a is omitted from FIG. 7 for clarity of illustration). FIGS. 10-12 illustrate the first drum 44a as a standalone element.

The first drum 44a can include a third thread 46a on an exterior surface thereof that can be configured to threadably mate with the first thread 42a of the second actuator 14, and the second drum 44b can include a fourth thread 46b on an exterior surface thereof that can be configured to threadably mate with the second thread 42b of the second actuator 14. The third and fourth threads 46a, 46b can be independent from one another, as in this illustrated embodiment, with each of the third and fourth threads 46a, 46b defining separate paths. The third and fourth threads 46a, 46b can wind in opposite directions around their respective drums 44a, 44b, e.g., one left-handed and one right-handed, thereby facilitating their mating with the opposite right- and left-hands of the first and second threads 42a, 42b. The third and fourth threads 46a, 46b can have any length around their respective drums' exterior surfaces 44c, 44d. In an exemplary embodiment, the third and fourth threads 46a, 46b can have the same length around their respective drums' exterior surfaces, which can facilitate symmetrical articulation of the end effector 8. The third and fourth threads 46a, 46b in this illustrated embodiment includes protrusions configured to slidably mate with corresponding grooves (e.g., the grooves 42a, 42b), but in other embodiments, the third and fourth threads 46a, 46b can include grooves configured to slidably mate with corresponding protrusions.

In response to actuation of the second actuator 14, e.g., in response to a user's rotation of the second actuator 12, the second actuator 14 can be configured to rotate about a longitudinal axis A2 (shown in FIG. 9) thereof. As in this illustrated embodiment, the second actuator's longitudinal axis A2 can be coaxial with the shaft assembly's longitudinal axis A. The second actuator 14 can be configured to remain stationary along its longitudinal axis A2 during the rotation. In other words, the second actuator 14 can be configured to not move distally or proximally during its rotation. The rotation of the second actuator 14 can cause the first and second drums 44a, 44b disposed within the second actuator 14 and threadably engaged therewith (e.g., the first thread 42a threadably engaged with the third thread 46a, and the second thread 42b threadably engaged with the fourth thread 46b) to simultaneously move. The opposed threading of the first and second threads 42a, 42b, and their corresponding third and fourth threads 46a, 46b of the first and second drums 44a, 44b, can cause the first and second drums 44a, 44b to move in opposite directions. One of the first and second drums 44a, 44b can move proximally, and the other of the first and second drums 44a, 44b can move distally. The movement of the first and second drums 44a, 44b can include longitudinal translation along the second actuator's longitudinal axis A2, which as in this illustrated embodiment, can also be along the shaft assembly's longitudinal axis A. The first and second drums 44a, 44b can be configured to alternately move distally and proximally during the actuation of the second actuator 14. In other words, rotation of the second actuator 14 in a same direction, whether it be clockwise or counterclockwise, can cause the first drum 44a to first move distally and the second drum 44b to move proximally, and then cause the first and second drums 44a, 44b to switch directions so that the first drum 44a moves proximally and the second drum 44b moves distally. The first actuator shaft 26a can be operatively connected to the first drum 44a, as discussed herein, such that the movement of the first drum 44a can cause a force to be applied to the first actuator shaft 26a and thereby cause corresponding movement of the first actuator shaft 26a, e.g., longitudinal translation of the first drum 44a in a proximal direction can cause longitudinal translation of the first actuator shaft 26a in the proximal direction. The second actuator shaft 26b can be operatively connected to the second drum 44b, as discussed herein, such that the movement of the second drum 44b can cause a force to be applied to the second actuator shaft 26b and thereby cause corresponding movement of the second actuator shaft 26b, e.g., longitudinal translation of the second drum 44b in a distal direction can cause longitudinal translation of the second actuator shaft 26b in the distal direction. The movement of the first and second actuator shafts 26a, 26b can be configured to cause the end effector 8 to articulate. Examples of end effector articulation using movable drums are further described in previously mentioned U.S. patent application Ser. No. 14/658,944 entitled "Methods and Devices for Actuating Surgical Instruments" filed on Mar. 16, 2015.

Figure 7:
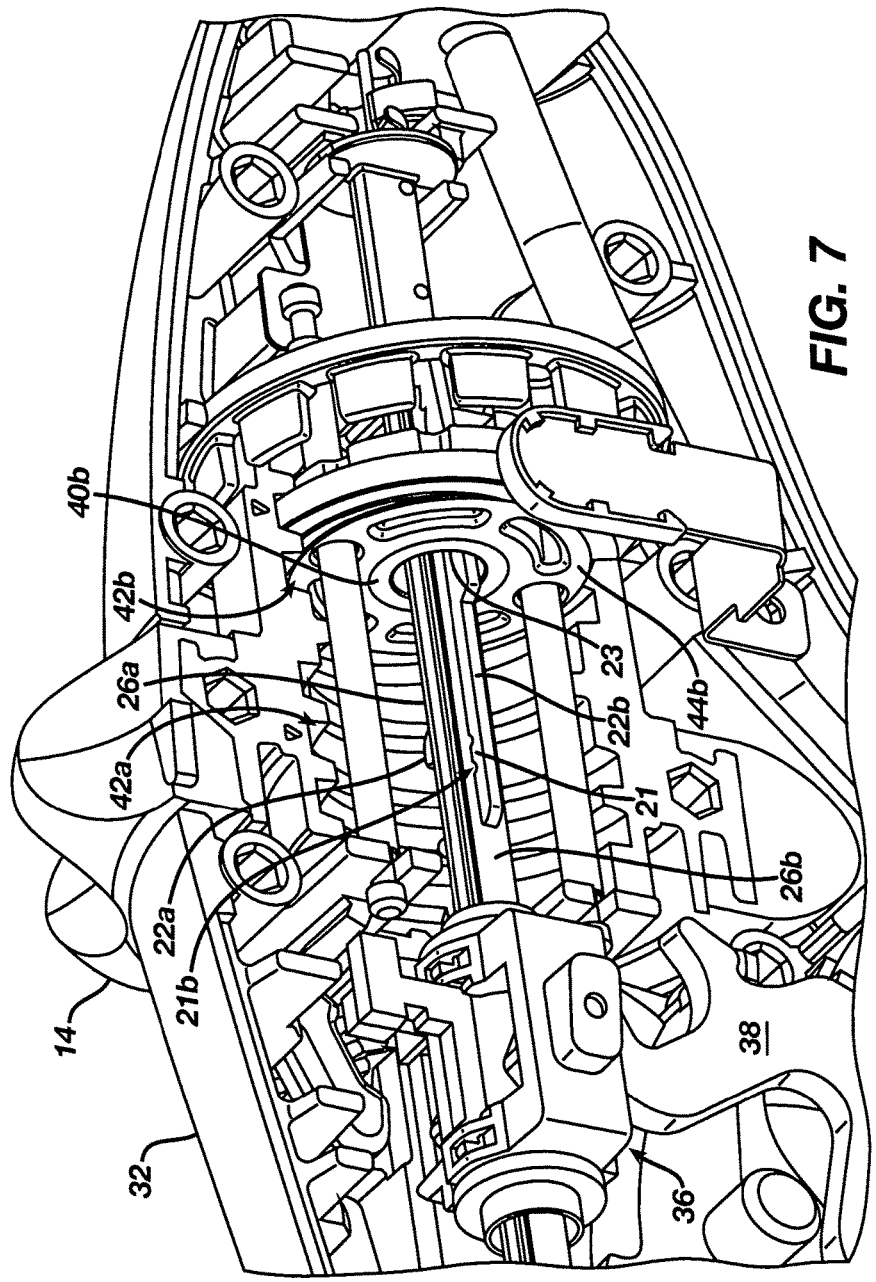
FIG. 7 is another perspective view of a portion of the handle portion of the device of FIG. 1 with select elements of the device omitted for clarity of illustration.
Figure 8:
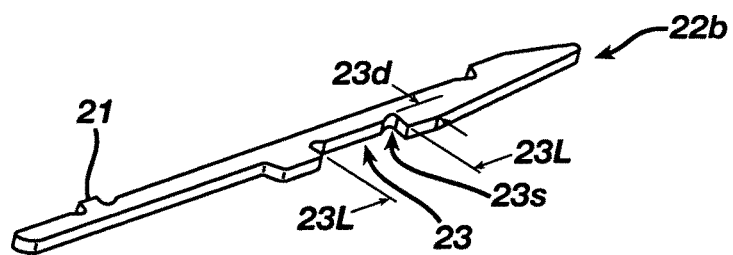
FIG. 8 is a perspective view of a connection rod of the device of FIG. 1.

The first actuator shaft 26a can be operatively connected to the first drum 44a and the second actuator shaft 26b can be operatively connected to the second drum 44b in a variety of ways. As in this illustrated embodiment, the device 2 can include the first connection rod 22a configured to couple the first actuation shaft 26a to the first drum 44a, and can include the second connection rod 22b configured to couple the second actuation shaft 26b to the second drum 44b. As shown in FIGS. 6-8, the second connection rod 22b can include a first mating element 21 configured to mate with a corresponding mating feature 21b of the second actuation shaft 26b. The first mating element 21 includes a protrusion and the mating feature 21b includes a hole in this illustrated embodiment, but the first mating element 21 and its corresponding mating feature 21b can have other configurations, e.g., the first mating element including a hole and the mating feature including a protrusion, one of the first mating element and the mating feature including a female connector and the other of the first mating element and the mating feature including a male connector, etc. The second connection rod 22b can include a second mating element 23 configured to mate with the second drum 44b. The second mating element 23 in this illustrated embodiment includes a longitudinal cut-out. The cut-out 23 can have a length 23L greater than a width of an inner diameter of the second drum 44b, thereby allowing the second connection rod 22b to extend through an inner passageway of the second drum 44b with the second drum 44b seated in the second connection rod's second mating element 23, as shown in FIGS. 6 and 7. The first connection rod 22a can similarly couple the first actuation shaft 26a to the first drum 44a with the first actuation shaft 26a extending through an inner passageway 44i of the first drum 44a, e.g., a third mating element (obscured in the figures) of the first connection rod 22a can be mated with a corresponding mating element (obscured in the figures) of the first actuation shaft 26a and a fourth mating element (obscured in the figures) of the first connection rod 22a can be mated with the first drum 44a.

Figure 14:
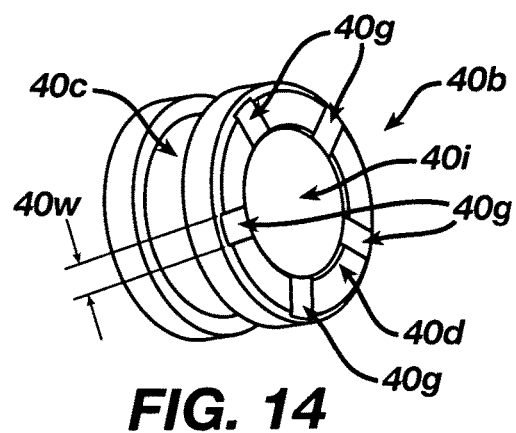
FIG. 14 is a perspective view of a friction member of the device of FIG. 1.
Figure 15:
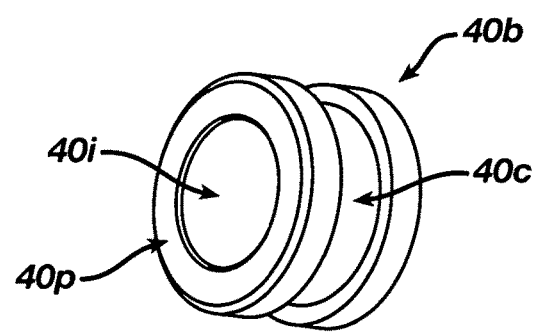
FIG. 15 is another perspective view of the friction member of FIG. 14.

The device 2 can include first and second friction members 40a, 40b, as shown in FIGS. 4-6 and 13 (the first friction member 40a is omitted from FIG. 6 for clarity of illustration). FIGS. 14 and 15 illustrate the second friction member 40b as a standalone element. The first and second friction members 40a, 40b can be configured to provide increased resistance to rotation of the shaft assembly 6, and the end effector 8 attached thereto, when the end effector 8 is articulated as compared to when the end effector 8 is not articulated. The first and second friction members 40a, 40b can thus be configured to increase rotational torque when the end effector 8 is articulated, e.g., is in the articulated position, as compared to when the end effector 8 is not articulated, e.g., is in the unarticulated position. In other words, the first and second friction members 40a, 40b can be configured to increase an amount of force required to rotate the shaft assembly 6, and the end effector 8 attached thereto, when the end effector 8 is articulated as compared to when the end effector 8 is not articulated. As mentioned above, the end effector 8 may thus be less likely to unintentionally rotate when articulated since a greater rotational torque force must be applied to the third actuator 18 to cause rotation of the shaft assembly 6 and end effector 8 when the end effector 8 is articulated as compared to when the end effector 8 is not articulated, which may allow for more precise control of end effector 8 position during performance of a surgical procedure and thus help the end effector 8 manipulate tissue as intended without losing grip on the tissue and/or without damaging any adjacent tissue or any other adjacent structures.

The first and second friction members 40a, 40b can have a variety of configurations. As shown in FIGS. 4-6 and 13-15, the second friction member 40b can include a generally cylindrical member having an inner passageway 40i extending therethrough. An exterior surface of the second friction member 40b can include a channel 40c formed therein around a circumference thereof. The channel 40c can be configured to seat the second drum 44b therein. A distal face 40d, e.g., a distal-facing rim, of the second friction member 40b can include a plurality of grooves 40g formed therein. The second friction member 40b includes five grooves 40g in this illustrated embodiment but can include another number of grooves. In an exemplary embodiment, the grooves 40g can be equidistantly spaced around the second friction member's circumference, as in this illustrated embodiment in which the grooves 40g are located at 0°, 72°, 144°, 216°, and 288° radially around the distal face 40d. The grooves 40b each have a rectangular shape in this illustrated embodiment, but the grooves 40b can have another shape. The grooves 40g in this illustrated embodiment each extend along a complete width of the friction member's distal face 40d, which may facilitate secure seating of the second connection rod 22b therein.

The second friction member 40b can be configured to be seated with the inner passageway of the second drum 44b such that the second actuation shaft 26b can extend through the inner passageway of the second drum 44b and the inner passageway 40i of the second friction member 40b. Each of the grooves 40g can be configured to seat therein the second connection bar 22b (e.g., a shelf 23s thereof) coupled to the second drum 44b through which the second connection bar 22b can also extend. A width 40w of each of the grooves 40g can be greater than a depth 23d of the shelf 23s (see FIGS. 8 and 14) of the second connection bar 22b configured to be alternately seated in and not seated in a groove 40g. The second connection bar 22b can thus be configured to be fully seated in one of the grooves 40g.

Whether one of the grooves 40g seats the second connection bar 22b at least partially therein or whether none of the grooves 40g seats the second connection bar 22b at least partially therein can depend on an amount of the end effector's articulation. When the end effector 8 is not articulated, none of the grooves 40g can seat the second connection bar 22b therein. An amount of rotational torque needed to rotate the shaft assembly 6 and the end effector 8, e.g., an amount of rotational torque needed to be applied to the third actuator 16 (e.g., an amount of manual force applied thereto by a user), can thus be at its lowest. The shaft assembly 6 and the end effector 8 may thus be easily rotated via actuation of the third actuator 16. When the end effector 8 is in the articulated position, one of the grooves 40g can seat the second connection bar 22b at least partially therein. The amount of rotational torque needed to rotate the shaft assembly 6 and the end effector 8 can thus be greater than when the end effector 8 is not articulated since the groove 40g in which the second connection rod 22b is at least partially seated can provide resistance to the rotational force. When the end effector 8 is articulated at a non-zero angle that is less than a maximum articulation angle of the end effector 8, one of the grooves 40g can seat the second connection bar 22b partially therein. The more that the end effector 8 is articulated, e.g., the greater the non-zero angle, the more of the second connection rod 22b that is seated in the groove 40g and thus the more resistance the second friction member 40b provides to rotation. When the end effector 8 is articulated at a non-zero angle that is the maximum articulation angle of the end effector 8, one of the grooves 40g can seat the second connection bar 22b fully therein. The second friction member 40b can thus be configured to provide maximum resistance to rotation when the end effector 8 is fully articulated. In this way, the rotational torque needed to rotate the shaft assembly 6 and the end effector 8 can increase in proportion to the amount of the end effector's articulation.

As shown in FIGS. 4, 6, and 15, a proximal face 40p, e.g., a proximal-facing rim, of the second friction member 40b can be free of grooves. In other embodiments, the second friction member's proximal face can include a plurality of grooves formed therein and the second friction member's distal face can be free of grooves, or each of the second friction member's proximal and distal faces can include a plurality of grooves. In embodiments in which both the proximal and distal faces include a plurality of grooves, a number of the grooves on the proximal and distal faces can be equal and the grooves can be radially aligned around the second friction member's circumference (e.g., placed at 0°, 60°, 120°, 180°, 240°, and 300° around the circumference on each of the proximal and distal faces) to facilitate simultaneous seating of the second connection bar 22b in one groove on each of the faces so frictional forces are balanced on the faces.

The first friction member 40a can be configured similar to the second friction member 40b, e.g., can have an inner passageway extending therethrough, can be configured to be seated in an inner passageway 44i of the first drum 44a, can include a circumferential channel 40h (see FIG. 4) configured to seat the first drum 44a therein, and can having a plurality of grooves 40r formed therein (in this illustrated embodiment, only in the first friction member's distal face) (two of the grooves 40r are obscured in FIG. 13) configured to seat the first connection bar 22a therein based on an amount of the end effector's articulation. A number of the grooves 40r, 40g on the first and second friction members 40a, 40b can be equal and the grooves 40r, 40g can be radially aligned around the first and second friction member's circumferences to facilitate simultaneous seating (partial or full) of the first and second connection bars 22a, 22b in their respective associated grooves 40r, 40g so frictional forces are balanced.

Figure 16:
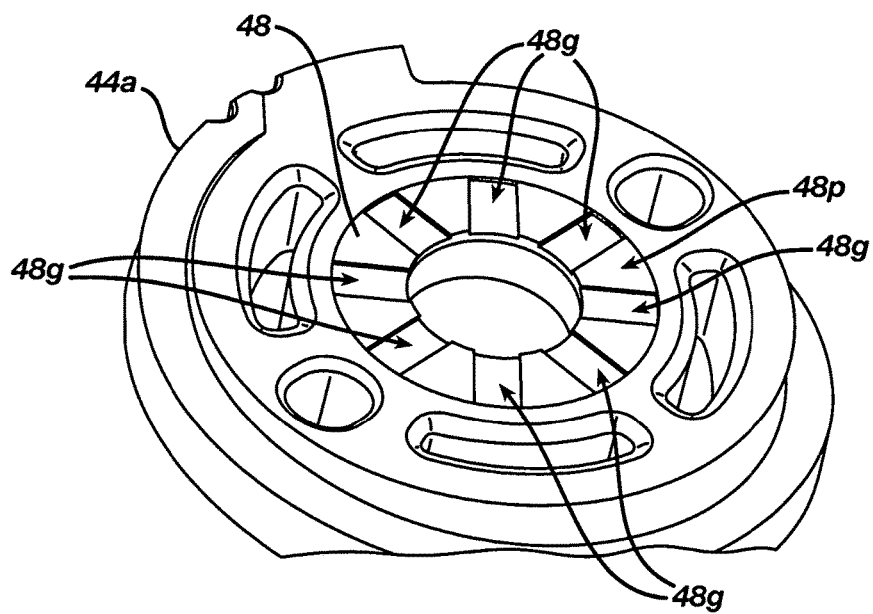
FIG. 16 is a perspective view of another embodiment of a friction member mated to the drum of FIG. 10.

FIG. 16 illustrates another embodiment of a friction member 48 that includes a plurality of grooves 48g, eight in this illustrated embodiment. The friction member 48 is shown in this illustrated embodiment positioned within the first drum 44a, but the friction member 48 can be coupled to other embodiments of drums. The grooves 48g in this illustrated embodiment each have a rectangular shape and each extend along a complete width of the friction member's proximal face 48p. As mentioned above, the friction member 48 can also include grooves on a distal face thereof or can only include the grooves 48g on the proximal face 48p.

Figure 17:
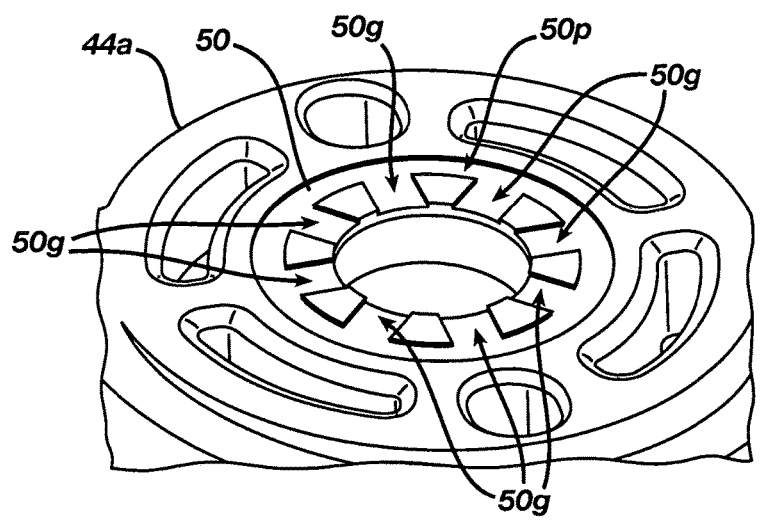
FIG. 17 is a perspective view of yet another embodiment of a friction member mated to the drum of FIG. 10.

FIG. 17 illustrates yet another embodiment of a friction member 50 that includes a plurality of grooves 50g, eight in this illustrated embodiment. The friction member 50 is shown in this illustrated embodiment positioned within the first drum 44a, but the friction member 50 can be coupled to other embodiments of drums. The grooves 50g in this illustrated embodiment each have a rectangular shape and each extend along a partial width of the friction member's proximal face 50p. Grooves extending along a partial width of a friction member's face, instead of along the complete width of the face, may facilitate manufacturing of the friction member, e.g., by facilitating stamping of the grooves into the face As mentioned above, the friction member 50 can also include grooves on a distal face thereof or can only include the grooves 50g on the proximal face 50p.

Referring again to the embodiment of FIG. 1, the first and second connection rods 22a, 22b can be configured to facilitate actuation of the second actuator 14, and hence facilitate articulation of the end effector 8, regardless of the rotational position of the shaft assembly 6 about the shaft assembly's longitudinal axis A. In other words, the third actuator 16 can be configured to be at any rotational position about the longitudinal axis A when the second actuator 14 is actuated to articulate the end effector 8. The rotation of the shaft assembly 6 can rotate the first and second actuation shafts 26a, 26b of the shaft assembly 6, as discussed herein, which adjusts the position of the first and second actuation shafts 26a, 26b relative to the second actuator 14 and to the actuation mechanism. The first and second connection rods 22a, 22b can be configured to rotate within and relative to their respective drums 44a, 44b and respective friction members 40a, 40b during rotation of the shaft assembly 6 and end effector 8 in response to actuation of the third actuator 16. Accordingly, regardless of the rotational position of the first and second connection rods 22a, 22b relative to their respective drums 44a, 44b and respective friction members 40a, 40b, the first and second actuation shafts 26a, 26b coupled to the first and second connection rods 22a, 22b can be moved proximally/distally in response to the proximal/distal movement of the drums 44a, 44b and their respective friction members 40a, 40b during actuation of the second actuator 14. Similar to the first and second connection rods 22a, 22b, the closure mechanism 36 can be configured to facilitate actuation of the first actuator 13, and hence facilitate movement of the cutting element, regardless of the rotational position of the shaft assembly 6 about the shaft assembly's longitudinal axis A.

Figure 18:
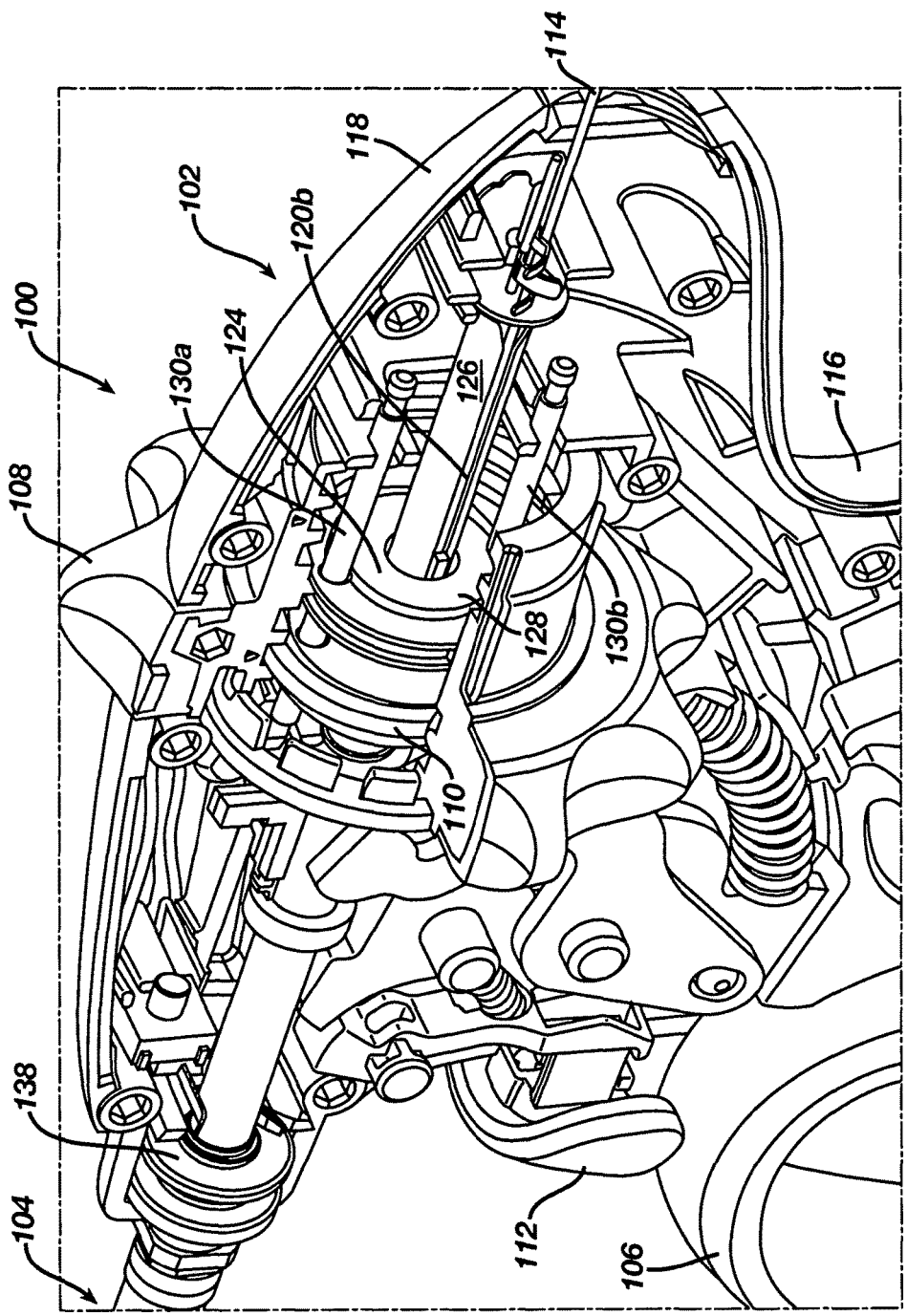
FIG. 18 is a perspective partially cross-sectional, partially transparent view of a portion of another embodiment of a surgical device.

FIG. 18 illustrates another embodiment of a surgical device 100. The device 100 can generally be configured and used similar to the surgical device 2 of the embodiment of FIG. 1 and similar to other embodiments of surgical devices described herein. The device 100 can include a proximal handle portion 102 including a main housing 118, a shaft assembly 104 extending distally from the handle portion 102, an end effector (not shown) including a pair of opposed jaws (or, in other embodiments, another type of working element) and being coupled to a distal end of the shaft assembly 104 at a pivot joint (not shown), electrodes (not shown), a first actuator 106 configured to effect the opening and closing of the opposed jaws and to effect movement of a cutting element (not shown) along the end effector, a second actuator 108 configured to effect articulation of the end effector, a third actuator (not shown) configured to rotate the shaft assembly 104 and the end effector about a longitudinal axis of the shaft assembly 104, a fourth actuator 112 configured to turn on and off the application of energy, an actuation mechanism operatively connected to the second actuator 108, a stationary handle 116, and a bend region (not shown).

The device 100 in this illustrated embodiment includes a conductive lead 114, which is in the form of an RF cable in this illustrated embodiment, and can hence be powered. In other embodiments, the surgical device can be unpowered, e.g., not be configured to apply energy to tissue.

Figure 19:
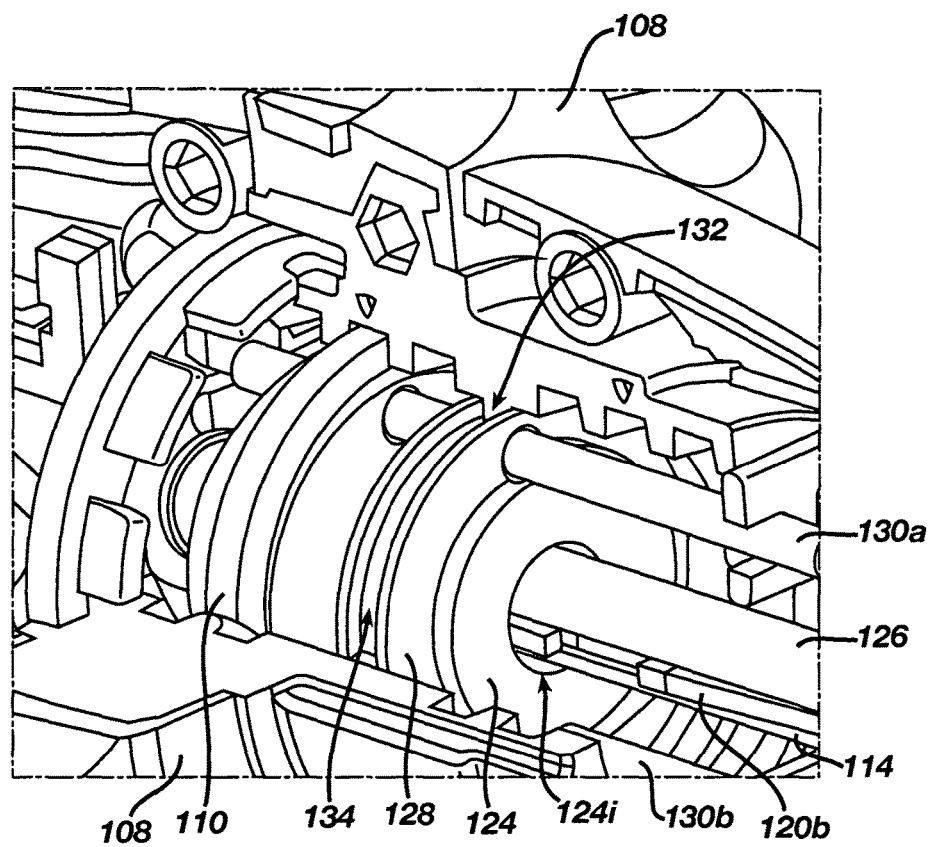
FIG. 19 is a perspective partially cross-sectional, partially transparent view of a handle portion of the device of FIG. 18.
Figure 20:
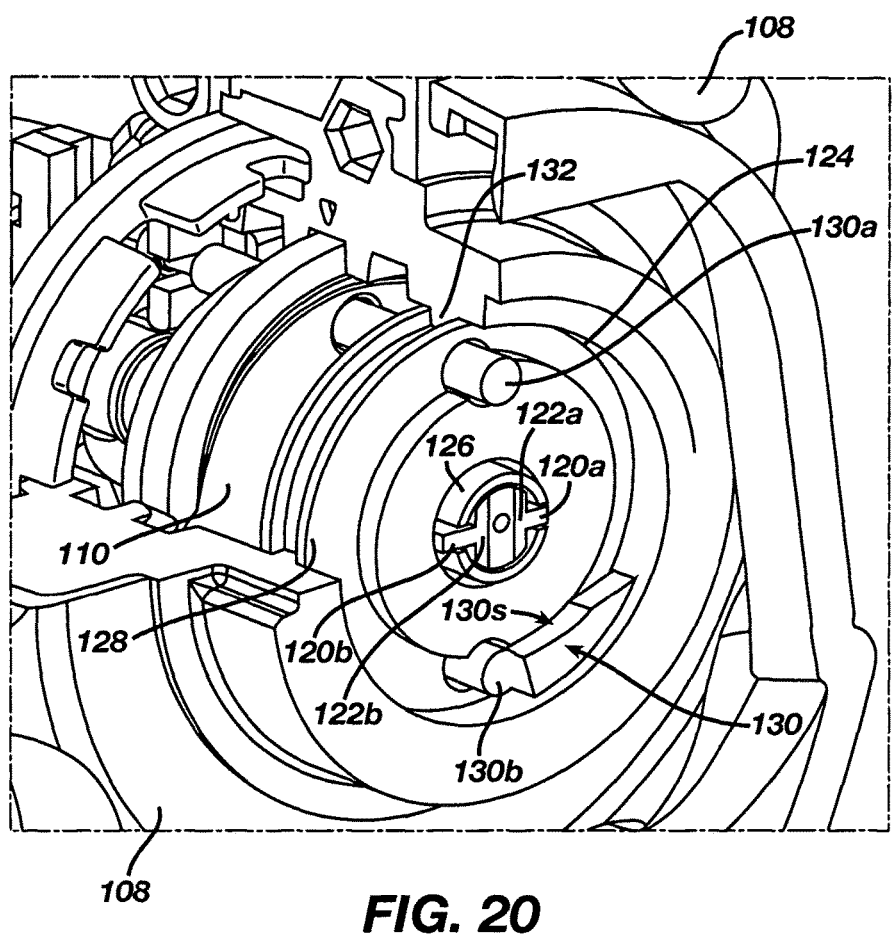
FIG. 20 is another perspective partially cross-sectional, partially transparent view of the handle portion of FIG. 19.

The second actuator 108 of the device 100 can be configured to effect articulation of the end effector similar to the second actuator 14 of the device 2 discussed above. As shown in FIGS. 18-20, the second actuator 108 can be operatively coupled to a first drum 110, a first connection rod 120a, a first actuation shaft 122a, a second drum (omitted from the figures for clarity of illustration), a second connection rod 120b, and a second actuation shaft 122b. Rotation of the second actuator 108 can cause the end effector to articulate due in response to motion of the drums 110, first and second connection rods 120a, 120b, and first and second actuation shafts 122a, 122b coupled thereto, similar to that discussed above regarding the second actuator 14 of the device 2 discussed above.

The device 100 can include a first friction member 124 associated with the first drum 110, the first connection rod 120a, and the first actuation shaft 122a. The device 100 can also include a second friction member (omitted from the figures for clarity of illustration) associated with the second drum, the second connection rod 120b, and the second actuation shaft 122b. The first and second friction members 124 can be configured to provide increased resistance to rotation of the shaft assembly 104, and the end effector attached thereto, when the end effector 8 is articulated as compared to when the end effector is not articulated, similar to the first and second friction members 40a, 40b discussed above. In this illustrated embodiment, the first and second friction members 124 each include a brake mechanism configured to apply an increased frictional force to an inner elongate shaft 126 of the shaft assembly 104 when the end effector is articulated as compared to when the end effector is not articulated. Thus, similar to the first and second friction members 40a, 40b discussed above, the first and second friction members 124 can be configured to increase rotational torque when the end effector is articulated, e.g., is in the articulated position, as compared to when the end effector is not articulated, e.g., is in the unarticulated position. In other words, the first and second friction members 124 can be configured to increase an amount of force required to rotate the shaft assembly 104, and the end effector attached thereto, when the end effector is articulated as compared to when the end effector is not articulated.

The first and second friction members 124 can have a variety of configurations. In general, the first and second friction members 124 can each be configured to deform in shape. The first and second friction members 124 can each be elastomeric, e.g., be made from one or more elastomeric materials (e.g., isoprene, silicone, etc.), to facilitate the shape deformation. The first and second friction members 124 can each be configured to deform in shape in response to pressure applied thereto by the second actuator 108, as discussed further below. In general, a degree of deformation of each of the first and second friction members 124 can correspond to an angle of the end effector's articulation and to an amount of rotational torque needed to rotate the shaft assembly 104 and the end effector. The greater the angle of end effector articulation (e.g., the closer the angle is to the end effector's maximum angle of articulation relative to the longitudinal axis of the shaft assembly 104), the greater the degree of deformation and the more rotational torque need be applied to the third actuator (e.g., an amount of manual force applied thereto by a user) to rotate the shaft assembly 104 and the end effector.

As shown in FIGS. 18-21, the first friction member 124 can be ring-shaped and can have an inner passageway 124i extending therethrough. The inner passageway 124i can have a first diameter when the first friction member 124 is in a first, default, non-compressed, non-deformed state. The first friction member 124 is shown in the first state in FIGS. 18-21. The diameter of the inner passageway 124i can be configured to become smaller in response to pressure applied to the first friction ring 124 such that the first friction member 124 is in a second, compressed, deformed state. The first friction member 124 is shown in the second state in FIG. 22.

The device 100 can include a first non-rotating member 128 configured to maintain the first friction member 124 in a fixed rotational position relative to the longitudinal axis of the shaft assembly 104. The first non-rotating member 128 can thus be configured to not rotate in response to rotation of the second actuator 104 and thereby not allow the first friction member 124 to rotate when the second actuator 104 rotates to articulate the end effector. As shown in FIGS. 18-22, the first non-rotating member 128 can be configured to be disposed within the second actuator 108. The first non-rotating member 128 can be configured to be at a fixed rotational position within the second actuator 108 and to be at a fixed axial position along the shaft assembly's longitudinal axis within the second actuator 108. The device 100 can include one or more guide pins 130a, 130b configured to couple to the first non-rotating member 128 to hold the first cam member 128 at a fixed rotational position. The second actuator 108 can include a circumferential rib 132 on an interior surface thereof that can be configured to be seated in a corresponding circumferential channel 134 formed in an exterior surface of the first non-rotating member 128. The rib 132 being circumferential may help hold the first non-rotating member 128 in a fixed axial position regardless of the rotational position of the second actuator 108 about the longitudinal axis of the shaft assembly 104.

The first non-rotating member 128 can be fixedly attached to the first friction member 124 and thereby be configured to maintain the first friction member 124 in a fixed rotational position within the second actuator 108. The first non-rotating member 128 and the first friction member 124 can be fixedly attached together in any of a variety of ways, as will be appreciated by a person skilled in the art, such as by adhesive, overmolding of the first friction member 124 to the first non-rotating member 128, friction fit, etc.

The second actuator 108 can include a first cam 130 on the interior surface thereof configured to selectively engage the first friction member 124. The engagement of the first cam 130 with the first friction member 124 can be configured to cause the first friction member 124 to deform in shape. In other words, the first cam 130 can be configured to apply pressure to the first friction member 124 to cause the first friction member 124 to deform in shape, e.g., to move from the first state to the second state or to move from one degree of deformation in the second state to another, greater degree of deformation in the second state. Similarly, release of the pressure applied to the first friction member 124 by the first cam 130 can cause the first friction member 124 to deform in shape, e.g., to move from the second state to the first state or to move from one degree of deformation in the second state to another, lesser degree of deformation in the second state. The first cam 130 can have an angled engagement surface 130s configured to engage the first friction member 124, which may allow the pressure applied to the first friction member 124 by the first cam 130 to increase in proportion to increased articulation of the end effector.

The second friction member can be configured similar to the first friction member 124, e.g., can be ring-shaped, can have an inner passageway extending therethrough, can be configured to move between first and second states, can be coupled to a second non-rotating member (not shown) that can be configured similar to the first non-rotating member 128, and can be configured to selectively engage a second cam (not shown) formed on the interior surface of the second actuator 108.

In at least some embodiments, instead of including both of the first and second friction members 124, the surgical device can instead only include the first friction member 124 or only the second friction member. Including only one of the friction members may reduce device cost and/or may ease device assembly.

Figure 21:
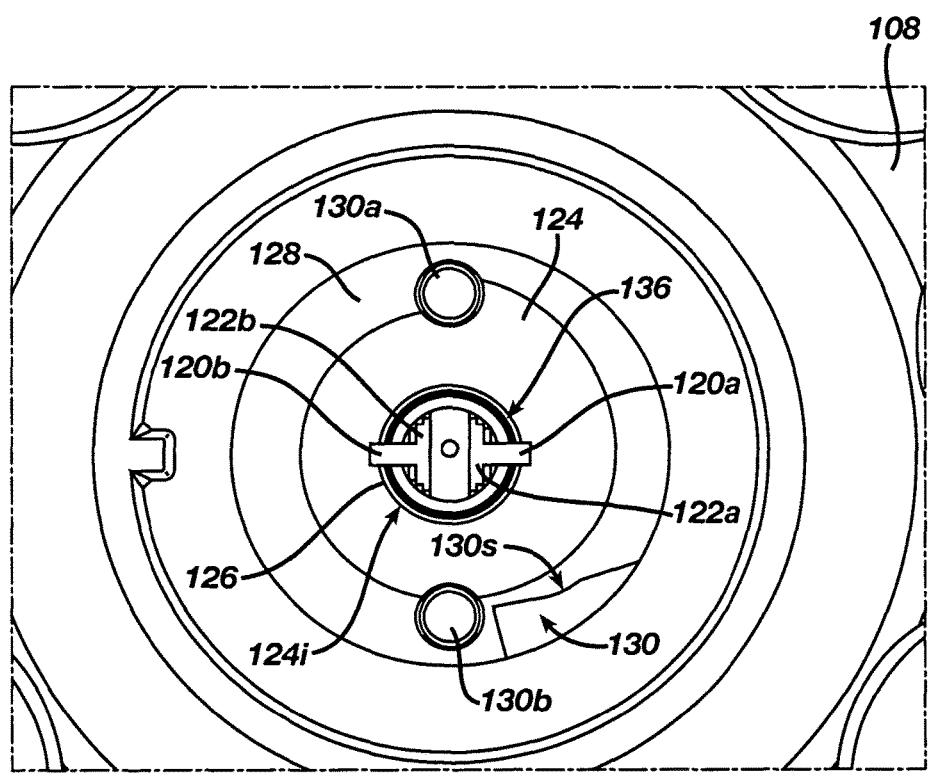
FIG. 21 is an end cross-sectional view of the device of FIG. 18 with an actuator thereof in a first position.
Figure 22:
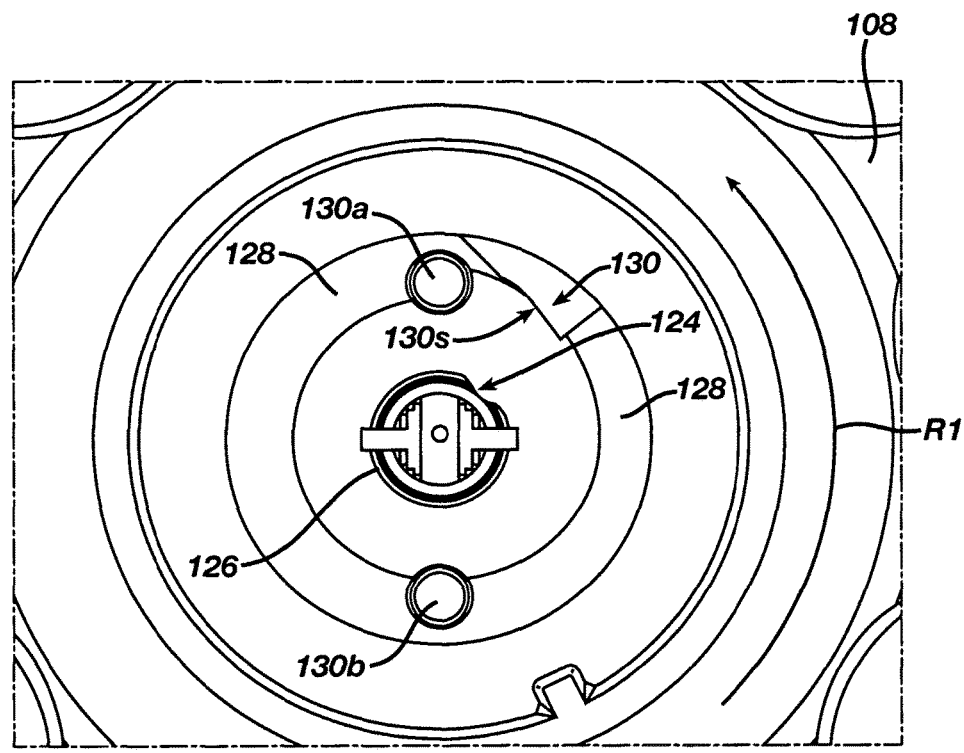
FIG. 22 is an end cross-sectional view of the device of FIG. 21 with the actuator in a second position.

FIGS. 21 and 22 illustrate an embodiment of the actuation of the second actuator 108, thereby causing movement of the first friction member 124 and causing movement of the first and second actuation shafts and, hence, causing angular movement of the end effector 8. FIG. 21 illustrates a first position of the second actuator 108 and the first friction member 124 in its first state, which corresponds to the end effector being in its unarticulated position, e.g., at a substantially zero angle relative to the longitudinal axis of the shaft assembly 104. With the first friction member 124 in its first state, the inner passageway 124i thereof can have a first minimum diameter such that a gap 136 exists between the inner elongate shaft 126 and the first friction member 124. The first cam 130 is disengaged from the first friction member 124, e.g., the engagement surface 130s thereof does not contact the first friction member 124, so as to not apply pressure thereto with the end effector in its unarticulated position, e.g., with the second actuator 108 in its first position.

FIG. 22 illustrates a second position of the second actuator 108 in which the second actuator 108 has been rotated from the first position of FIG. 21, e.g., rotated counterclockwise as shown by arrow R1. The rotation of the second actuator 108 has caused the first drum 110 to move distally and the second drum to move proximally. The first drum 110 has moved within the second actuator 108 due to its threaded engagement with the second actuator's first thread, and the second drum has moved within the second actuator 108 due to its threaded engagement with the second actuator's second thread. The distal movement of the first drum 110 has caused the first actuation shaft operatively connected thereto to correspondingly move distally. Similarly, the proximal movement of the second drum has caused the second actuation shaft operatively connected thereto to correspondingly move proximally. The end effector has accordingly articulated to the left from its position in FIG. 21. The first non-rotating member 128 has not moved in response to the actuation of the second actuator 108 between FIGS. 21 and 22.

The rotational movement of the second actuator 108 from FIG. 21 to FIG. 22 has caused the first cam 130, e.g., the engagement surface 130s thereof, to engage the first friction member 124 and apply pressure thereto. The first friction member 124 has accordingly deformed in shape, as shown in FIG. 22. The first friction member 124 has moved into the gap 136 to press against the exterior surface of the inner elongate shaft 126, and the minimum diameter of the first friction member 124 has decreased to a second minimum diameter that is less than the first minimum diameter. A rotational torque required to rotate the inner elongate shaft 126, and hence the shaft assembly 104 and the end effector, is thus greater than in FIG. 21 due to the frictional force applied by the first friction member 124 to the inner elongate shaft 126. As mentioned above, due to the angled engagement surface 130s of the first cam 130, the more that the second actuator 108 is rotated from its first position, e.g., the more that the end effector is angled from its unarticulated position, the more pressure is exerted by the first cam 130 on the first friction member 124 and hence the more force is needed to be applied to the third actuator to rotate the shaft assembly 104 and the end effector.

The second friction member is not shown in FIGS. 21 and 22 but can move similarly to the first friction member 124 in response to the actuation of the second actuator 108.

Figure 23:
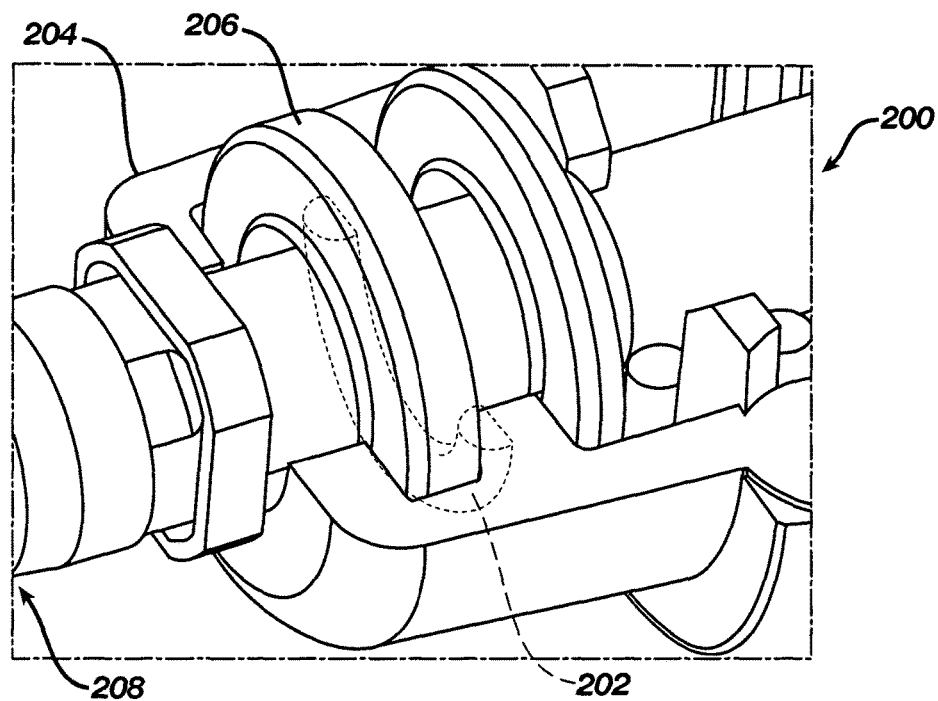
FIG. 23 is a perspective partially transparent view of a portion of another embodiment of a surgical device.
Figure 24:
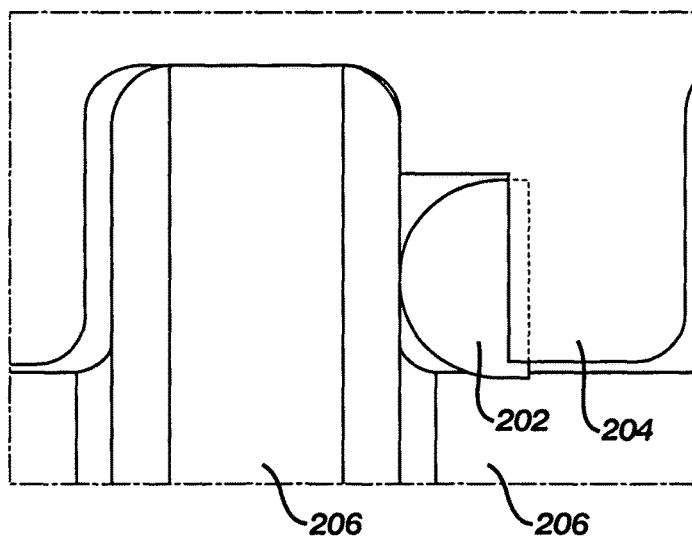
FIG. 24 is a cross-sectional view of a portion of the device of FIG. 23.

FIGS. 23 and 24 illustrate another embodiment of a surgical device 200 that includes a friction member 202 in the form of a brake mechanism. The device 200 can generally be configured and used similar to the surgical device 100 of the embodiment of FIG. 18 and similar to other embodiments of surgical devices described herein. In this illustrated embodiment, the friction member 202 is not disposed within the device's second actuator, e.g., the actuator configured to cause end effector articulation, with the device's handle portion 204. Instead, the friction member 202 is disposed elsewhere within the device's handle portion 204.

The device 200 can include a shaft connector 206 at least partially disposed within the handle portion 204 that can be configured to facilitate connection of a shaft assembly 208 of the device 200 to the handle portion 204. In response to articulation of an end effector (not shown) at a distal end of the shaft assembly 208 from an unarticulated position to an articulated position, the shaft connector 206 can be configured to move in a proximal direction. Similarly, in response to articulation of the end effector from the articulated position to the unarticulated position, the shaft connector 206 can be configured to move in a distal direction.

The friction member 202 can, as in this illustrated embodiment, be positioned within the handle portion 204 adjacent to the shaft assembly 208. By way of comparison, a similarly located and configured shaft connector 138 of the device 100 is shown in FIG. 18.

In response to the end effector being further articulated (e.g., moved from the unarticulated position to the articulated position or moved from one articulated position to a more articulated position), the proximal movement of the shaft assembly 208 can apply pressure to the friction member 202 and thereby deform a shape of the friction member 202 and cause the friction member 202 to exert force on the shaft assembly 208. Thus, similar to that discussed above regarding the friction members of the device 100, the friction member 202 can be configured to provide increased resistance to rotation of the shaft assembly 208, and the end effector attached thereto, when the end effector is articulated as compared to when the end effector is not articulated. Similarly, in response to the end effector's articulation being reduced (e.g., moved from the articulated position to the unarticulated position or articulated from one articulated position to a less articulated position), the distal movement of the shaft assembly 208 can apply less pressure to the friction member 202 and thereby deform a shape of the friction member 202 and cause the friction member 202 to exert less force on the shaft assembly 208. In an exemplary embodiment, the friction member 202 can be configured to exert no force on the shaft assembly 208 when the end effector is in the unarticulated position, which may ease rotation of the shaft assembly 208 and the end effector when the end effector is not articulated.

The friction member 202 has a half ring shape in this illustrated embodiment, but the friction member 202 can have other shapes, e.g., a full ring shape, a sphere, etc.

Figure 25:
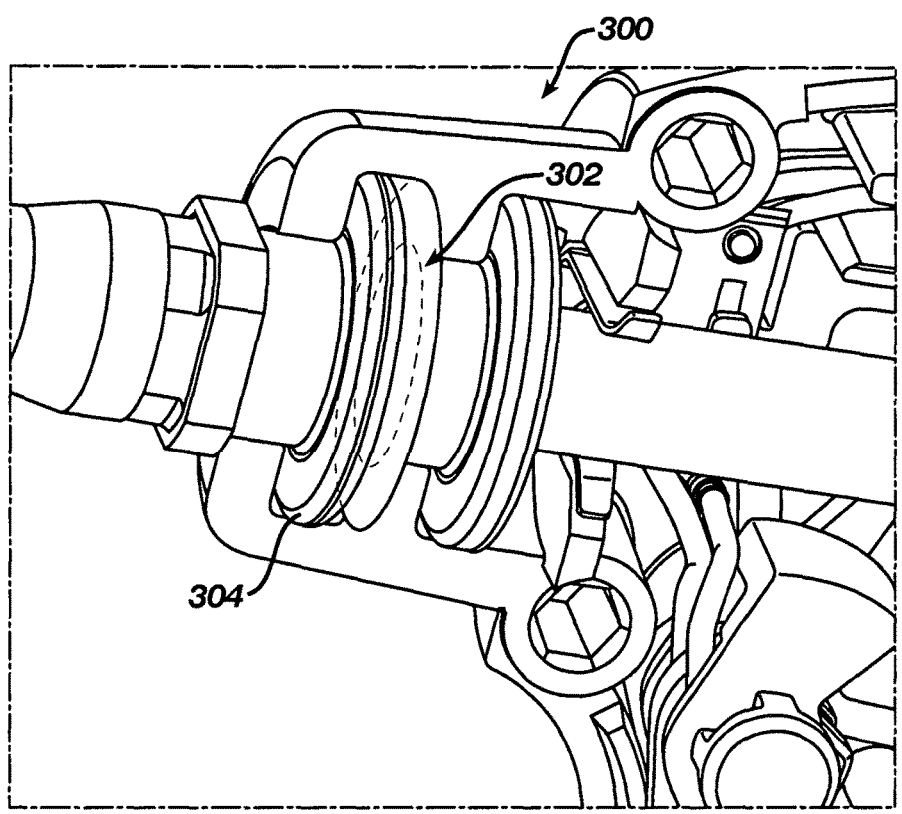
FIG. 25 is a perspective partially cross-sectional, partially transparent view of another embodiment of a surgical device.

FIG. 25 illustrates yet another embodiment of a surgical device 300 that includes a friction member 302 in the form of a brake mechanism. The device 300 can generally be configured and used similar to the surgical device 200 of the embodiment of FIGS. 23 and 24. In this illustrated embodiment, the friction member 302 disposed adjacent a shaft connector 204 has a ring shape, as opposed to the half ring shape of the friction member 202 of FIGS. 23 and 24.

Figure 26:
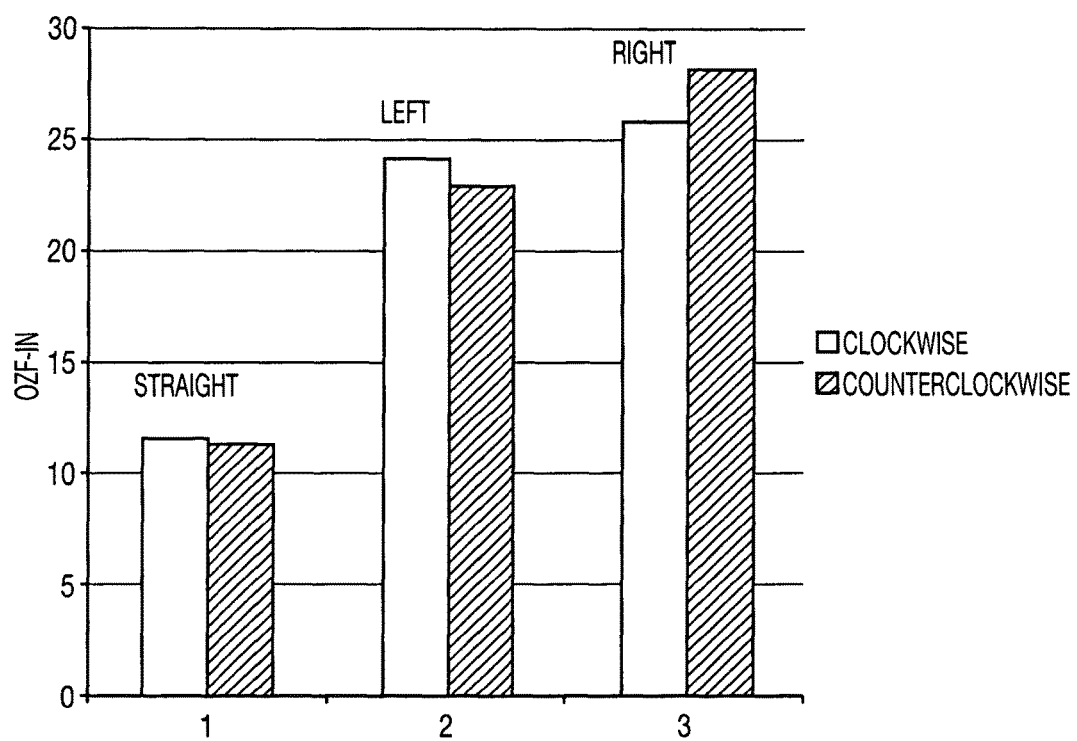
FIG. 26 is a graph showing test results for the device of FIG. 23.

FIG. 26 illustrates test results for the friction member 202 of FIGS. 23 and 24 for an example in which the friction member 202 is made from Morris Technology DM_9510 Grey80_Shore 65 material and is configured to be compressed 0.005 inches. As shown in FIG. 25, a force (in ounce force inches) required to rotate the shaft assembly 208 and end effector, clockwise or counterclockwise, when the end effector is unarticulated (labeled "Straight" in FIG. 25) is less than the force required to rotate the shaft assembly 208 and end effector, clockwise or counterclockwise, when the end effector is articulated Left or Right.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
    a handle;
    an elongate shaft extending distally from the handle and being configured to rotate relative to the handle;
    an end effector at a distal end of the elongate shaft and having first and second jaws configured to engage tissue therebetween, the end effector being configured to articulate relative to the elongate shaft such that the end effector is angularly oriented relative to the elongate shaft;
    a friction member disposed within the handle and configured to resist rotation of the elongate shaft when the end effector is articulated relative to the elongate shaft; and
    an actuator configured to be actuated to cause rotational movement of the actuator and thereby cause the articulation of the end effector;
    wherein, when the end effector is articulated relative to the elongate shaft, a force required to rotate the elongate shaft relative to the handle is greater than a force required to rotate the elongate shaft relative to the handle when the end effector is in a non-articulated, substantially linear orientation relative to the elongate shaft; and
    wherein the friction member is operatively coupled to the actuator such that the rotational movement of the actuator causes rotational movement of the friction member.

2. The device of claim 1, wherein the friction member is configured to apply an increased frictional force to the elongate shaft when the end effector is articulated as compared to when the end effector is in the non-articulated, substantially linear orientation.

3. The device of claim 2, wherein the frictional force is configured to increase in proportion to increasing articulation of the end effector.

4. The device of claim 1, wherein the friction member is configured to increasingly deform in shape in proportion to increasing articulation of the end effector.

5. The device of claim 1, wherein the friction member is elastomeric.

6. The device of claim 1, wherein the actuation of the actuator also causes compression of the friction member.

7. The device of claim 1, further comprising a second actuator configured to be actuated to cause the rotation of the elongate shaft;

wherein the force required to rotate the elongate shaft relative to the handle when the end effector is articulated relative to the elongate shaft is applied to the second actuator, and the force required to rotate the elongate shaft relative to the handle when the end effector is in the non-articulated, substantially linear orientation relative to the elongate shaft is applied to the second actuator such that a greater force is required to be applied to the second actuator to rotate the elongate shaft when the end effector is articulated relative to the elongate shaft.

8. The device of claim 1, wherein the friction member is configured to not resist rotation of the elongate shaft when the end effector is in the non-articulated, substantially linear orientation.

9. The device of claim 1, wherein the actuator is configured to move relative to the elongate shaft;
wherein the friction member has one or more grooves formed therein that are configured to be locked with the actuator when the end effector is articulated relative to the elongate shaft and to be unlocked from the actuator when the end effector is in the non-articulated, substantially linear orientation.

10. The device of claim 1, wherein the end effector is configured to rotate with the elongate shaft relative to the handle.

11. A surgical device, comprising:
an elongate shaft having a longitudinal axis;
an end effector at a distal end of the elongate shaft, the end effector being configured to manipulate tissue during performance of a surgical procedure;
a first actuator configured to be actuated to cause rotation of the elongate shaft and the end effector about the longitudinal axis of the elongate shaft;
a second actuator configured to be actuated to angularly adjust the end effector relative to the longitudinal axis of the elongate shaft; and
a friction member configured to adjust an amount of force required to be applied to the first actuator to cause the rotation of the elongate shaft and the end effector based on an angle of the end effector relative to the longitudinal axis of the elongate shaft; and
wherein the friction member includes a clutch mechanism configured to move between a locked configuration and an unlocked configuration based on the angle of the end effector relative to the longitudinal axis of the elongate shaft, the amount of force corresponding to whether the clutch mechanism is in the locked configuration or the unlocked configuration.

12. The device of claim 11, wherein the greater the angle of the end effector relative to the longitudinal axis of the elongate shaft, the greater the amount of force the friction member is configured to require to be applied to the first actuator to cause the rotation of the elongate shaft and the end effector.

13. The device of claim 11, further comprising a handle, the elongate shaft extending distally from the handle, and the friction member being disposed within the handle.

14. A surgical device, comprising:
a handle;
an elongate shaft extending distally from the handle and being configured to rotate relative to the handle;
an end effector at a distal end of the elongate shaft and having first and second jaws configured to engage tissue therebetween, the end effector being configured to articulate relative to the elongate shaft such that the end effector is angularly oriented relative to the elongate shaft;
a first actuator configured to be actuated to cause the articulation of the end effector;
a friction member disposed within the handle and configured to apply an increased frictional force to the elongate shaft when the end effector is articulated as compared to when the end effector is in a non-articulated, substantially linear orientation relative to the elongate shaft;
a second actuator configured to be actuated to cause rotation of the elongate shaft and the end effector relative to the handle; and
a rod operatively coupled to the second actuator such that actuation of the second actuator causes the rod to rotate relative to the friction member;
wherein the friction member has a groove formed therein that is configured to seat the rod therein;
wherein when the end effector is in the non-articulated, substantially linear orientation, the rod is not seat in the groove;
wherein when the end effector is articulated, the rod is at least partially seated in the groove; and
wherein the rotation of the rod causes the rod to move between being not seated in the groove and being at least partially seated in the groove.

* * * * *